(12) United States Patent
Sinko et al.

(10) Patent No.: US 9,125,835 B2
(45) Date of Patent: Sep. 8, 2015

(54) SYNERGISTIC COMBINATIONS TO REDUCE PARTICLE DOSE FOR TARGETED TREATMENT OF CANCER AND ITS METASTASES

(75) Inventors: Patrick J. Sinko, Annandale, NJ (US); Jieming Gao, New Brunswick, NJ (US); Manjeet Deshmukh, Edison, NJ (US); Xiaoping Zhang, Edison, NJ (US); Matthew S. Palombo, Marmora, NJ (US); Sherif Ibrahim, Old Bridge, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 55 days.

(21) Appl. No.: 13/296,203

(22) Filed: Nov. 14, 2011

(65) Prior Publication Data

US 2012/0183621 A1    Jul. 19, 2012

Related U.S. Application Data

(60) Provisional application No. 61/413,368, filed on Nov. 12, 2010.

(51) Int. Cl.

| | |
|---|---|
| *A61K 31/385* | (2006.01) |
| *A61K 9/51* | (2006.01) |
| *A61K 31/337* | (2006.01) |
| *A61K 31/4745* | (2006.01) |
| *A61K 31/65* | (2006.01) |
| *B82Y 5/00* | (2011.01) |
| *A61K 45/06* | (2006.01) |
| *A61K 31/519* | (2006.01) |
| *A61K 31/555* | (2006.01) |
| *A61K 31/675* | (2006.01) |
| *A61K 31/704* | (2006.01) |
| *C08G 65/329* | (2006.01) |

(52) U.S. Cl.
CPC ............ *A61K 9/5146* (2013.01); *A61K 31/337* (2013.01); *A61K 31/385* (2013.01); *A61K 31/4745* (2013.01); *A61K 31/519* (2013.01); *A61K 31/555* (2013.01); *A61K 31/65* (2013.01); *A61K 31/675* (2013.01); *A61K 31/704* (2013.01); *A61K 45/06* (2013.01); *B82Y 5/00* (2013.01); *C08G 65/329* (2013.01); *C08L 2203/02* (2013.01)

(58) Field of Classification Search
CPC . A61K 9/5146; A61K 31/337; A61K 31/704; A61K 31/675; A61K 31/555; A61K 31/519; A61K 45/06; A61K 31/65; A61K 31/4745; A61K 31/385; A61K 2300/00; C08L 2203/02; C08G 65/329; B82Y 5/00
USPC .................. 424/497; 514/283, 440; 525/403; 977/788, 906
See application file for complete search history.

(56) References Cited

U.S. PATENT DOCUMENTS

| | | | |
|---|---|---|---|
| 6,294,204 B1 * | 9/2001 | Rossling et al. .............. | 424/497 |
| 2005/0043215 A1 | 2/2005 | Minko et al. | |
| 2005/0196343 A1 * | 9/2005 | Reddy et al. ............... | 424/9.322 |
| 2008/0260725 A1 * | 10/2008 | Naik et al. ................. | 424/130.1 |
| 2008/0280813 A1 | 11/2008 | Minko et al. | |
| 2008/0317870 A1 * | 12/2008 | Ray et al. ...................... | 424/649 |
| 2011/0117024 A1 | 5/2011 | Sinko et al. | |
| 2011/0268803 A1 | 11/2011 | Prud'homme et al. | |

OTHER PUBLICATIONS

Linda Strandberg Ihrlund, et al, 3-Bromopyruvate as Inhibitor of Tumor Cell Energy Metabolism and Chemopotentiator of Platinum Drugs, 2 Mol. Oncol. 94 (2008).*
Ken Olaussen, et al, DNA Repair by ERCC1 in Non-Small-Cell Lung Cancer and Cisplatin-Based Adjuvant Chemotherapy, 355 N Engl. J Med. 983 (2006).*
Gang Ruan & Si-Shen Feng, Preparation and Characterization of Poly(lactic acid)-poly(ethylene glycol)-poly(lactic acid) (PLA-PEG-PLA) Microspheres for Controlled Release of Paclitaxel, 24 Biomat. 5037 (2003).*
Subbu Venkatraman, et al, Micelle-like Nanoparticles of PLA-PEG-PLA Triblock Copolymer as Chemotherapeutic Carrier, 298 Intl. J Pharmaceut. 219 (2005).*
C. Gedlicka, et al, Amelioration of Docetaxel/Cisplatin Induced Polyneuropathy by α-Lipoic Acid, 14 Ann. Oncol. 339 (2003).*
Eric L. Snyder, et al, Enhanced Targeting and Killing of Tumor Cells Expressing the CXC Chemokine Receptor 4 by Transducible Anti-cancer Peptides, 65 Cancer Res. 10646 (2005).*
Alvarez, R. et al., Immunotherapy of ovarian cancer, Expert Opin. Biol. Ther. 2(4) (2002), 409-417 (abstract only).
Dass, Cr. et al., Particle-mediated intravascular delivery of oligoneucleotides to tumors: associated biology and lessons from genotherapy, Drug Deliv. 8(4) (2001), 191-213 (abstract only).
Fennelly, D., Dose Intensity in Advanced Ovarian Cancer: Have We Answered the Question?, Clinical Cancer Research, vol. 1, (1995), 575-582.

(Continued)

*Primary Examiner* — Sean Basquill
(74) *Attorney, Agent, or Firm* — Fox Rothschild LLP

(57) ABSTRACT

Non-Small Cell Lung Carcinomas (NSCLCs) are treated with Gel Micro-Particles (GMPs) that passively accumulate in the lungs and contain Nano-Particles (NPs) combining one or more therapeutic agents that are cytotoxic to the NSCLC with one or more NSCLC active targeting ligands, as well as one or more other optional agents that increase cellular uptake, enhance the pro-apoptotic effect of the chemotherapeutic agent(s), and the like. NPs targeting other cancer cells are also disclosed, as well as NP-containing GMPs that reduce the occurrence of tumor metastasis.

13 Claims, 14 Drawing Sheets
(6 of 14 Drawing Sheet(s) Filed in Color)

(56) References Cited

OTHER PUBLICATIONS

Goodrich, K. et al., Measurement of the Modulus and Yield Strength of Soft Gels: Experiments and Numerical-Simulation, Journal of Rheology 33, 317-327 (abstract only).

Hanjani, P. et al., Phase II evaluation of 3-day topotecan with cyclophosphamide in the treatment of recurrent ovarian cancer, Gynecol. Oncol. 85(2) (2002), 278-284 (abstract only).

Kobayashi, M. et al., Circadian chemotherapy for gynecological and genitourinary cancers, Chronobiol. Int. 19(1) (2002), 237-251 (abstract only).

Kopecek, J. et al., Water soluble polymers in tumor targeted delivery, Journal of Controlled Release 74 (2001) 147-158.

Kunath, K. et al., HPMA copolymer-anticancer drug-OV-TL16 antibody conjugates.3. The effect of free and polymer-bound adriamycin on the expression of some genes in the OVARCAR-3 human ovarian carcinoma cell line, Eur. J. Pharm. Biopharm. Jan. 2000:49 11-15 (abstract only).

Markman, M. et al., Phase II Trial of Weekly Single-Agent Paclitaxel in Platinum/Paclitaxel-Refractory Ovarian Cancer, Journal of Clinical Oncology, vol. 20, No. 9 (2002) 2365-2369.

Minko, T. et al., Advanced Drug Delivery Systems in Cancer Chemotherapy, Disease Management and Clinical Outcomes, 3:48-54 (2001).

Ross, R.W. et al., Osteoporosis in men treated with androgen deprivation therapy for prostate cancer, J. Urol. 167(5), 1952-1956 (2002) (abstract only).

Sehouli, J. et al., First-line chemotherapy with weekly paclitaxel and carboplatin for advanced ovarian cancer: a phase I study, Gynecol. Oncol. 85(2) (2002) 321-326 (abstract only).

Narumi, T. et al., Synthesis and biological evaluation of selective CXCR4 antogonists containing alkene dipeptide isosteres, Org Biomol Chem. Feb. 7, 2010;8 (3): 616-21 (abstract only).

Vasey, P.A. et al., Phase I trial of intraperitoneal injection of the E1B-55-kd-gene deleted adenovirous ONYX-015 (dl1520) given on days 1 through 5 every 3 weeks in patients with recurrent/refractory epithelial ovarian cancer, J. Clin. Oncol. Mar. 15, 2002:20(6),1562-1569 (abstract only).

\* cited by examiner

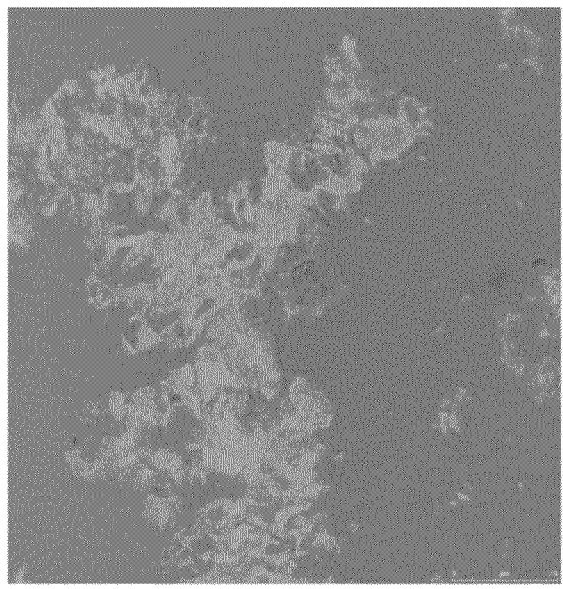 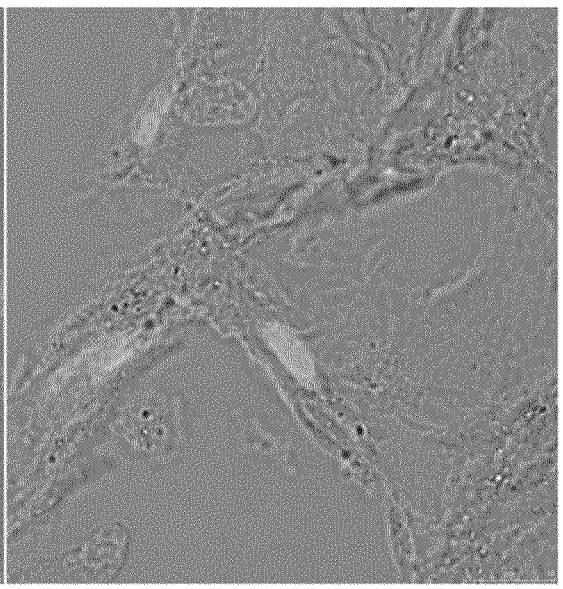
FIG. 4

FIGS. 7(a), (b), (c), and (d)

SYNERGISTIC COMBINATIONS TO REDUCE PARTICLE DOSE FOR TARGETED TREATMENT OF CANCER AND ITS METASTASES

CROSS REFERENCE TO RELATED APPLICATIONS

The instant application claims 35 U.S.C. §119(e) priority to U.S. Provisional Patent Application Ser. No. 61/413,368 filed Nov. 12, 2010, the disclosure of which is incorporated by reference herein.

STATEMENT REGARDING FEDERALLY FUNDED RESEARCH

This invention was made with government support under Grant A1051214 awarded by the National Institutes of Health. Accordingly, the U.S. Government has certain rights in this invention.

FIELD OF THE INVENTION

The present invention relates to a lung-targeted nanoparticle ("NP")/gel micro-particle ("GMP") delivery system for the treatment of non-small cell lung cancer ("NSCLS").

BACKGROUND OF THE INVENTION

A central issue in cancer chemotherapy is the severe toxic side effects of anticancer agents on healthy tissues, which invariably imposes dose reduction, treatment delay or even discontinuance of therapy (Fennelly (1995) Clin. Cancer Res. 1:575-582; Hanjani, et al. (2002) Gynecol. Oncol. 85:278-284; Kobayashi, et al. (2002) Chronobiol. Int. 19:237-251; Ross and Small (2002) J. Urol. 167:1952-1956; Markman, et al. (2002) J. Clin. Oncol. 20:2365-2369; Sehouli, et al. (2002) Gynecol. Oncol. 85:321-326). Cytotoxicity for healthy organs can be significantly diminished by employing a drug delivery system which targets cancer cells (Alvarez, et al. (2002) Expert. Opin. Biol. Ther. 2:409-417; Dass and Su (2001) Drug Deliv. 8:191-213; Kopecek, et al. (2001) J. Controlled Rel. 74:147-158; Kunath, et al. (2000) Eur. J. Pharm. Biopharm. 49:11-15; Minko, et al. (2001) Dis. Manag. Clin. Outcomes 3:48-54; Vasey, et al. (2002) J. Clin. Oncol. 20:1562-1569). The usage of these drug delivery systems prevents, in most cases, the uptake of the drug by normal cells and enhances the influx and retention of the drug in cancer cells.

NSCLC remains one of the leading causes of cancer-related mortality worldwide. NSCLC represents a heterogeneous group of diseases that are often classified together due to similarities in diagnosis, prognosis and treatment. The standard-of-care with an anticancer agent paclitaxel and a platinum drug extends life only minimally due to drug-related toxicities, poor treatment/prevention of metastases, and resistance. Increasing drug doses in order to boost tissue concentrations is not feasible due to cytotoxic effects and low solubility.

The lung is the only organ in the body that accepts the entire venous blood output from the heart. Since it is the first capillary bed encountered by the venous blood, it is in a singular position to entrap a wide variety of particles. "Passive" drug targeting to the lung (i.e., accumulation) can be achieved by taking advantage of this natural flow-filtration phenomenon. In 1964, human serum albumin "macroaggregates" ("MAA") exhibiting suitable size and degradation properties became the first MPs approved for IV injection and lung targeting. Two approved products remain on the market today as pulmonary perfusion diagnostic agents, Pulmolite® (CIS-US) and Draximage® (Draxis). There are not any products for delivering drugs to the lung that exploit this established and safe pathway. The rationale for passive lung accumulation is compelling—MAA product and MPs are efficiently entrapped (>90%) after a single injection as compared to only 5-20% of an inhaled dose. In addition, inhalers must be used multiple times daily but a single IV injection may provide effective treatment for up to one week. Size and deformability are the two major determinants of the passive accumulation and retention of MPs in the lung.

In addition to these factors, toxicity is also influenced by the total particle dose. Presently, approved human MAA dosages are much lower (<0.2 mg or ~350,000 MPs) than the corresponding LD50 in animals (43.8 mg/kg to 82.6 mg/kg) suggesting that tolerable human MP doses may be significantly higher than what is currently used in the diagnostic product. It has been estimated that only ~0.6% of available (i.e., opened) capillary vessels are occluded immediately following administration of 1×106 albumin aggregates (4 times the current human MAA dose). About 33% of all pulmonary capillaries are normally collapsed and not available (the main reason for this is that lung blood pressure is about ⅙ of systemic blood pressure). When micro-occlusions occur, collapsed capillaries are recruited in order to maintain normal physiological perfusion conditions. Therefore, the maximum tolerated dose of MPs in humans is higher than current MAA doses and in the milligram range.

While targeted drug delivery is an effective approach for improving drug concentrations, the options for lung targeting are narrow. The inherently low absorption and poor lung distribution associated with inhalation are further diminished as a result of reduced lung function in NSCLC patients. Despite recent advances in molecular characterization and targeted and adjuvant therapies, surgical resection remains the mainstay of curative treatment. Unfortunately, less than one third of NSCLC patients present with resectable disease. Neoadjuvant chemotherapy alone or with concurrent radiation is often used for stage IIIA NSCLC but is often tried in patients with stage IIIB and at times in patients with stage I or II disease. The general prognosis of NSCLC patients remains poor and unpredictable due to the high invasiveness potential of the disease. However, after the initial diagnosis, more than half of the patients with localized lung cancer survive at least 5 years. Therefore, an alternative delivery approach that targets primary lung tumors and controls metastasis is urgently needed.

SUMMARY OF THE INVENTION

One aspect of the present invention is directed to a method of inducing tumor cell death in a patient by administering to said patient an effective amount of one or more chemotherapeutic agents that are cytotoxic to said tumor cells and one of more chemopotentiators for at least one of said chemotherapeutic agents so that simultaneous uptake by said tumor cells of said one or more chemopotentiator and one or more chemotherapeutic agent occurs. This method may further utilize a carrying agent to administer said one or more chemopotentiator and one or more chemotherapeutic agent. The carrying agent may be a nanoparticle having a cell-surface targeting moiety, and, in certain embodiments, the cell-surface targeting moiety is DV3. Additionally, the nanoparticle may be embedded in a gel microparticle.

The chemopotentiator used in the present invention may be selected from the group consisting of alpha-lipoic acid, alpha-lipoic acid analogues, sodium-r-alpha lipoate, dichloroacetate, carnosine, flavin mononucleotide, flavin adenine dinucleotide, ubiquinone, idebenone, mitochondrial uncouplers, emthylsulfonylmethane, monophenols, flavonoids, phenolic acids, hydroxycinnamic acids, lignans, tyrosol esters, carotenoids, monoterpenes, saponins, lipids, betalains, organosulfides, indoles, glucosinolates, sulfur compounds, organic acids, tocohperols, tocotrienols, vitamin D, vitamin D analogues, potassium iodide, iodine, selenium, zinc, aspirin, ibuprofen, naproxen, indomethacin, celecoxib, sulindac, diclofenac, eicosapentaenoic acid, docosahexaenoic acid, alpha linolenic acid, gamma linolenic acid, ricinoleic acid, curcumin, resveratrol, quercetin, lutein, and lycopene.

The chemotherapeutic agent used in the present invention may be selected from the group consisting of campothecin, paclitaxel, topotecan, Taxol, Cytochalasin B, Gramicidin D, Ethidium Bromide, Emetine, Mitomycin, Etoposide, Tenoposide, Vincristine, Vinblastine, Colchicin, Doxorubicin, Daunorubicin, Mitoxantrone, Mithramycin, Actinomycin D, 1-Dehydrotestosterone, Glucocorticoids, Procaine, Tetracaine, Lidocaine, Propranolol, and Puromycin and analogs or homologs thereof.

In another aspect, the present invention is directed to a method for inhibiting cancer metastasis in a subject diagnosed with cancer by administering an effective amount of ligand surface functionalized nanoparticles targeted to bind with one or more chemokine receptors to said subject. In certain embodiments, the ligand can be DV3.

In yet another aspect, the present invention is directed to a method for inhibiting cancer metastasis in a subject diagnosed with cancer by administering an effective amount of one or more inhibitors to said subject, wherein said inhibitors target one or more pro-metastatic signaling factors. This method may further utilize a carrying agent to administer said one or more chemopotentiator and one or more chemotherapeutic agent. The carrying agent may be a nanoparticle having a cell-surface targeting moiety, and, in certain embodiments, the cell-surface targeting moiety is DV3. Additionally, in certain embodiments, the pro-metastatic signaling factor is selected from the group consisting of nuclear factor kappa-light-chain-enhancer of activated B cells, extracellular-signal-regulated kinases, and matrix metallopeptidase 9.

In yet another aspect, the present invention is directed to a composition for in vivo delivery of a chemotherapeutic agent and a chemopotentiator comprising a polymeric nanoparticle carrier loaded with said chemotherapeutic agent and said chemopotentiator. In certain embodiments, a gel microparticle is loaded with said polymeric nanoparticle carrier. In one embodiment, the loading of the polymeric nanoparticle carrier comprises a physical admixture of said polymeric nanoparticle carrier, said chemotherapeutic agent and said chemopotentiator. In another embodiment, the loading of the polymeric nanoparticle carrier comprises covalently attaching said chemotherapeutic agent and said chemopotentiator to an interior of, or a surface of the polymeric nanoparticle carrier. In certain embodiments, the loading of the gel microparticle may comprise a physical admixture of said gel microparticle and said polymeric nanoparticle carrier, or may comprise covalently attaching said polymeric nanoparticle carrier to said gel microparticle. In other embodiments, the polymeric nanoparticle carrier, the chemotherapeutic agent, and the chemopotentiator are physically admixed by flash nanoprecipitation.

In certain embodiments, the polymeric nanoparticle carrier comprises a polyethylene glycol coating, wherein the ends of the polyethylene glycols are functionalized for with targeting ligands. In another embodiment, the polymeric nanoparticle carrier is a polyethylene glycol-based dendron.

In a certain embodiment, the chemopotentiator of the composition is selected from the group consisting of alpha-lipoic acid, alpha-lipoic acid analogues, sodium-r-alpha lipoate, dichloroacetate, carnosine, flavin mononucleotide, flavin adenine dinucleotide, ubiquinone, idebenone, mitochondrial uncouplers, emthylsulfonylmethane, monophenols, flavonoids, phenolic acids, hydroxycinnamic acids, lignans, tyrosol esters, carotenoids, monoterpenes, saponins, lipids, betalains, organosulfides, indoles, glucosinolates, sulfur compounds, organic acids, tocohperols, tocotrienols, vitamin D, vitamin D analogues, potassium iodide, iodine, selenium, zinc, aspirin, ibuprofen, naproxen, indomethacin, celecoxib, sulindac, diclofenac, eicosapentaenoic acid, docosahexaenoic acid, alpha linolenic acid, gamma linolenic acid, ricinoleic acid, curcumin, resveratrol, quercetin, lutein, and lycopene; and the chemotherapeutic agent of the composition is selected from the group consisting of campothecin, paclitaxel, topotecan, Taxol, Cytochalasin B, Gramicidin D, Ethidium Bromide, Emetine, Mitomycin, Etoposide, Tenoposide, Vincristine, Vinblastine, Colchicin, Doxorubicin, Daunoru-bicin, Mitoxantrone, Mithramycin, Actinomycin D, 1-Dehydrotestosterone, Glucocorticoids, Procaine, Tetracaine, Lidocaine, Propranolol, and Puromycin and analogs or homologs thereof.

In certain embodiments, polymeric nanoparticle carrier of the composition is surface-functionalized with DV3 ligand targeted to bind with one or more pro-metastatic chemokine signaling factor receptors on a NSCLC cell.

The present invention discloses at least two levels of targeting. The first level is passive targeting. GMPs selectively accumulate in the lung after IV administration. Applicants' data demonstrates that passive targeting achieves a 10-fold increase in anti-cancer drug potency in the lung and 10-fold lower peak systemic drug concentrations.

The second level is active targeting. Two types of NPs are used to achieve active targeting. High drug loading into NPs is achieved using a novel fabrication process that overcomes the solubility limits of hydrophobic cancer drugs. The NP surfaces are functionalized with ligands that selectively target cancer cells. The second NP group is also functionalized with cell surface ligands, however, instead of delivering drug cargo selectively inside the cancer cell, these NPs are engineered to tightly bind to cancer cell surface receptors and remain there in order to inhibit the metastatic signaling cascade. Once GMPs passively accumulate in the lung, NPs imbedded in the GMP matrix diffuse out and seek cancer cells. The dual targeting approach results in extraordinary specificity of treatment and an additional 10-fold reduction in effective drug concentrations.

In summary, the delivery approaches described in the present invention are highly innovative for several reasons: (1) they challenge current treatment approaches by proposing chemotherapy for earlier stage disease specifically to minimize the probability of metastatic spread (i.e., keep and treat the disease locally in the lung), (2) the passive targeting approach is a novel method to achieve effective lung drug concentrations while minimizing systemic exposure (i.e., it has been used in humans but only for diagnostics), (3) the active targeting approach using the chemokine targeting ligand has previously only been attempted for a different objective (i.e., it was used in vitro for an anticancer prodrug), (4) while the National Cancer Institute ("NCI") considers CPT a high priority drug, it has failed in the clinic and requires a delivery approach such as that of the present invention to successfully bring it to the clinic and (5) imbedding NPs into GMPs using microfluidics has not been previously reported.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 4 shows fluorescently labeled ANPs (left panel) injected intravenously (16 mg/kg) into rats. The right panel illustrates the accumulation of ANPs in the lung capillaries of the rats.

FIG. 14 (b) displays a Maldi-TOF spectrum G3 PEG-based dendrimer. The detected and calculated molecular weights are 12240.3 D and 12260 D, respectively.

DETAILED DESCRIPTION

Figure 1:
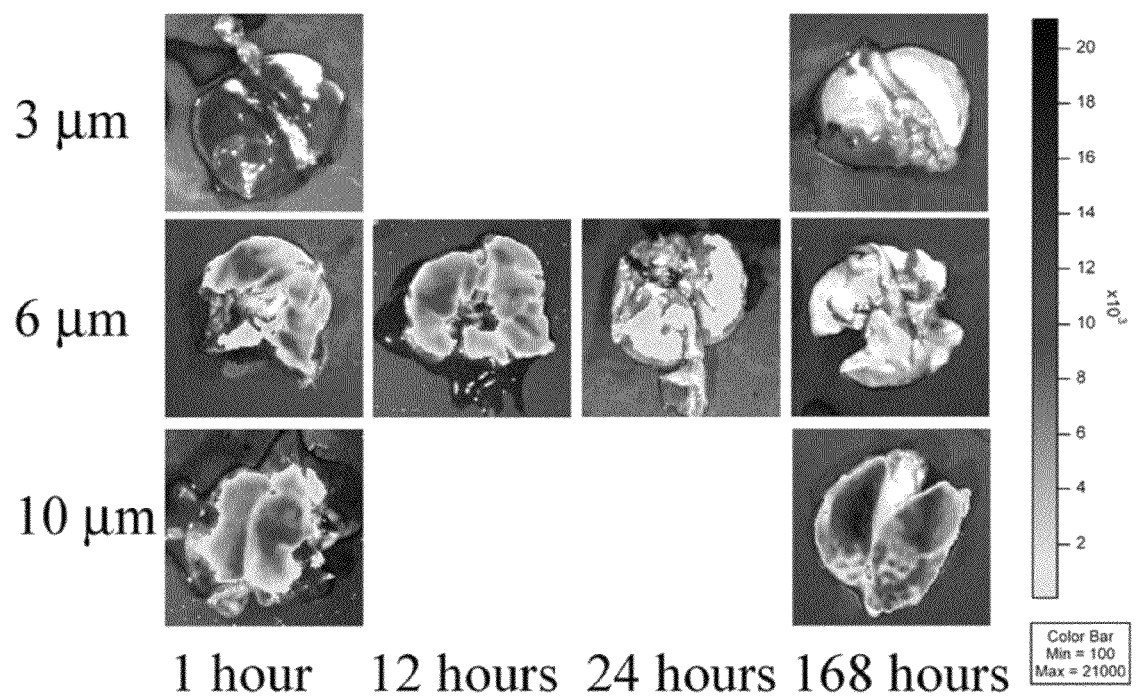
FIG. 1 shows passive lung accumulation of IV injected 3, 6 and 10 μm fluorescently labeled polystyrene MPs in healthy rats.

Chemotherapeutic agents are known to induce programmed cell death or apoptosis. The activation of cellular anti-apoptotic defenses that prevent the translation of drug-induced damage into cell death is a key factor in cellular, non-pump resistance to a broad spectrum of anticancer drugs. Thus, a net increase in apoptosis induction during cancer treatment could significantly increase cancer cell death and the efficacy of chemotherapy. Moreover, targeting an anticancer agent specifically to cancer cells has numerous benefits including the maintenance of a low blood-to-cell concentration ratio in order to reduce therapy-limiting side effects and increase anticancer effectiveness.

While specific molecules are provided herein, these molecules are illustrative examples of the inventive composition and should not be construed as limitations thereof. It is contemplated that various combinations of each component in the active targeting embodiment can be tailored to include specific anticancer agents or cell-surface targeting moieties known to have activity or receptors, respectively, in specific cancers. The active targeting aspect of the present invention useful in treating cancers including, but not limited to, skin cancer, ovarian cancer, breast cancer, cervical cancer, colorectal cancer, prostate cancer, liver cancer, lung cancer, stomach cancer, bone cancer, and pancreatic cancer. In particular embodiments of the invention employing passive targeting alone or in combination with active targeting, the cancer is a lung cancer such as non-small cell lung cancer (NSCLC).

The dual-level targeting approach of the present invention for the treatment of lung cancer is highly significant for at least two reasons. First, it achieves effective lung drug concentrations while minimizing systemic exposure and toxicity in healthy tissues. It is generally recognized that new neoadjuvant regimens with reduced toxicity are needed. Treatment options that reduce the duration of platinum-based chemotherapy while improving quality of life and progression-free survival are considered a high priority. The dual-level targeting approach results in an extraordinary degree of lung specificity. The first level of targeting (i.e., passive) is critical since the injection of free NPs leads to widespread body distribution and extravasation into non target tissues. Passive accumulation deposits GMPs directly into the lung thus limiting total body distribution of drug-bearing NPs. This is particularly important given the lack of complete ligand-receptor specificity and the distribution of receptors in organs other than the target organ. Thus, the multifunctional delivery system addresses two critical barriers to achieving effective treatment of NSCLC: (1) it provides highly efficient lung targeting in order to achieve local sustained drug concentrations and minimal systemic exposure to maximize therapeutic efficacy while minimizing side effects and (2) it provides a platinum-free drug regimen.

Another reason that the delivery system of the present invention is highly significant is that it offers an early chemotherapeutic approach for limiting metastatic spread. Metastasis consists of a series of sequential steps, all of which must be successfully completed. These include shedding of cells from a primary tumor into the circulation, survival of the cells in the circulation, arrest in a new organ, extravasation into the surrounding tissue, initiation and maintenance of growth and vascularization of the metastatic tumor. The early stages of metastasis (i.e., cell shedding, survival in the circulation and extravasation into tissue) are very efficient. However, the later stages of metastasis (i.e., maintenance of growth and vascularization) are very inefficient primarily due to the regulation of cancer-cell growth in secondary sites. Therefore, it is imperative that treatment options include methods that inhibit early stage metastatic processes in the lung because the "seeds" are constantly and efficiently produced and disseminated from the primary lung tumor to sites of metastasis.

Critical elements in targeting early metastasis in the lung are the chemokine receptors CXCR4 and CXCR7. The expression of the chemokine receptor CXCR4 is associated with NSCLC metastases and shorter survival times. Recently, CXCR7 was also linked to NSCLC metastasis. Activation of CXCR4 or CXCR7 induces NSCLC cell migration and adhesion to stromal cells that secrete CXCL12, which in turn provides growth-and drug resistance-signals to the tumor cells. CXCR4 antagonists disrupt CXCR4-mediated cell-adhesion to stromal cells as well as sensitize cells to cytotoxic drugs and thereby antagonize cell adhesion-mediated drug resistance. Specifically, activation of CXCR4 by CXCL12 triggers downstream signaling cascades that upregulate NF-κB, ERK and MMP-9. Increased MMP activity of tumor cells correlates with a higher invasive and metastatic potential. Therefore another important aspect of the present invention involves inhibition of the chemokine receptors CXCR 4/7 or their downstream signaling factors that promote metastasis. This represents a major breakthrough because NSCLC metastasis is the major cause of morbidity and mortality for this disease.

In one embodiment of the present invention, a Method of inducing tumor cell death in a patient in need thereof administers to the patient effective amounts of one or more chemopotentiators and one or more chemotherapeutic agents so that simultaneous uptake of the one or more chemopotentiator and one or more chemotherapeutic agent occurs. This method can be achieved by first utilizing a series of GMPs that achieve (a) optimal passive lung targeting efficiency, retention and elimination and (b) minimal pulmonary toxicity (structural and functional alterations and inflammation). Second, embedded within the GMP matrix is a series of carrying agents, such as a nanoparticles ("NP"), having functionalized surfaces for active targeting.

Regarding passive targeting, systemic administration of microparticles ("MPs") is an efficient alternative to inhalation for delivery to the lungs. Passive pulmonary targeting offers two significant advantages over inhalation: (1) very high localization efficiency (95% versus about 15%) and (2) wide distribution and penetration into the deep lung.

An embodiment of the present invention includes a delivery system comprising GMP, a plurality of NPs loaded within the GMP, and one or more drugs loaded within the NPs. For the purposes of this application, the term loaded is defined as including physical admixtures of biocompatible polymeric nanoparticles and compounds for particle delivery, and the covalent attachment of compounds to the interior of, or surface of the NPs. U.S. Pat. No. 7,846,893 and U.S. Patent Appl. Pub. No. 2011/0117024 disclose methods by which the loaded NPs of the present invention may be prepared. Another NP suitable for use in the present invention is disclosed in the patent application entitled "POLYETHYLENE GLYCOL-BASED DENDRONS" filed on the same day the present patent application, and claiming priority to U.S. Patent Application Ser. No. 61/413,352, filed Nov. 12, 2010. U.S. Patent Appl. Pub. No. 2011/0268803 discloses the method by which the dual level targeting system of the present invention may be prepared and GMP-NP combinations suitable for use with the present invention. The contents of all three publications are and the concurrently-filed patent application are incorporated herein by reference. A delivery system may also include at least one of one or more targeting agent or one or more chemopotentiator.

An embodiment includes NPs as drug "sources" and uses thereof. In the presence of a lipophilic sink, the drug molecules, encapsulated in the NP, may partition into the matrix of the GMPs and diffuse to the sink.

As disclosed in U.S. Patent Appl. Pub. No. 2011/0268803, the GMPs may include degradable linkages between individual polymers of a co-polymer. The degradable linkages between polymers in GM Ps can be, but are not limited to, ester degradable linkages, ketal degradable linkages, acetal degradable linkages, enzymatically degradable linkages, linkages degraded by reducing or oxidizing reactions and degradable orthoester linkages. The degradable linkages in GMPs can be all of one kind or more than one kind. The more than one kind can be selected from the preceding degradable linkages. GMPs may have any suitable size to be retained in a target capillary. GMPs may have a size of about 1 µm to 60 µm.

The shear modulus of a microparticle may be any value, but could be selected in combination with the particle size to optimize retention in the desired site of therapeutic action. In one embodiment, the shear modulus of a GMPs may be between 4 Pa and 200,000 Pa. In other embodiments, shear modulus of a GMPs may have any integer value from 4 Pa to 200,000 Pa. In still other embodiments, the shear modulus of GMPs may be in a range between and including any two integer values from 4 Pa to 200,000 Pa, or may have any value in a range between and including any two integer values from 4 Pa to 200,000 Pa. The shear modulus of the MP may be determined by forming a gel using the same chemical formulation as in the dispersed phase of the emulsion, polymerizing said gel phase, and measuring the shear modulus or storage modulus of the gel using rheological instrumentation such as are standard in the materials characterization field. Measurements of this type are described in Goodrich, K., A. Yoshimura, et al. Measurement of the Modulus and Yield Strength of Soft Gels-Experiments and Numerical-Simulation (1989) Journal of Rheology 33(2): 317-327, which is incorporated herein by reference as if fully set forth.

The GMPs may include biocompatible, aqueous-soluble polymers. The GMPs may include functionalized, crosslinkable, biocompatible polymers. The GMPs may include polymers formed from functionalized poly(2hydroxyethyl methacrylate) polymers. The GMPs may include polymers formed from functionalized polyphosphate polymers. The GMPs may include polymers formed from functionalized PEG polymers or copolymers. The GMPs may include polymers formed from functionalized dextran polymers. The GMPs may include polymers formed from functionalized polyvinyl pyrrolidone polymers or co-polymers. The GMPs may include polymers formed from functionalized polyacrylic acid polymers or copolymers. The GMPs may include polymers formed from functionalized poly(amine) or poly(amide) polymers or copolymers. Examples of these include but are not limited to DMAEMA and NIPAam. NIPAam may be utilized to provide temperature sensitive moieties.

Applicants have determined that optimal threshold size for passive pulmonary targeting and retention of rigid MPs is about 6 µm. By way of example, this was demonstrated by intra-venous ("IV") administration of rigid internally labeled fluorescent polystyrene MPs of various sizes (2, 3, 6 and 10 µm) to male Sprague Dawley rats. Total lung retention, biodistribution and intra-lung distribution were assessed using either a fluorescent plate reader or a Xenogen IVIS 100 Imaging System ("IVIS"). Complete entrapment and retention of 10 µm MPs was observed for the one-week duration of the study, whereas 2 µm and 3 µm MPs readily passed through the lung. 80% of the 6 µm MPs were retained for the first 2 days with 15% being slowly cleared over the next 5 days suggesting a possible threshold size for rigid MPs (FIG. 1). 6 µm and 10 µm MPs were widely distributed throughout lung tissue with evidence of entrapment in pulmonary capillaries but not arterioles. This demonstrated that rigid 6 µm MPs transiently but efficiently target the pulmonary capillaries. However, any of the sizes disclosed by U.S. Patent Appl. Pub. No. 2011/0268803 are suitable for use with the present invention.

Applicants have further determined that the size threshold for passive pulmonary targeting of highly deformable MPs is about 30 µm. This determination was provided for by the investigation of passive lung targeting and retention of highly deformable, micron-sized aggregated nanogel particles ("ANP"). However, any of the sizes disclosed by U.S. Patent Appl. Pub. No. 2011/0268803 are suitable for use with the present invention.

As disclosed by U.S. Patent Appl. Pub. No. 2011/0268803, GMPs of precisely tailored sizes and tailored deformabilities can be fabricated using microfluidics. Microfluidics ("MF") is the rapidly developing field of using flow geometries at the micron scale to enable control of chemical reactions, crystallization, diagnostics and particle formation. Advances in the field have helped to clarify the conditions required to break fluid streams into uniform micron-sized droplets. The smallest, most uniform drops are made by techniques involving "flow focusing" in which an outer sheath flow stretches the fluid filament and causes breakup as shown schematically in FIGS. 7(a) and (b) with an image of 6 µm drops being produced by flow focusing. Using MF technologies, Applicants have demonstrated the ability to fabricate GMPs of controlled softness or deformability. The GMPs made to validate the approach are shown in FIG. 7(c) and (d). FIG. 7(c) shows PEG polymerized GMPs with an average size of 8 µm containing 100 nm NPs containing fluorescent dye showing the successful production of NPs encapsulated in GMPs. FIG. 7(d) shows a time-lapse image of PEG polymerized 25 µm GMPs being forced through a 20 µm contraction as a model of capture in the lung capillaries.

U.S. Patent Appl. Pub. No. 2011/0268803 discloses that in one embodiment GMPs are formed by polymerizing PEG macromers with molecular weights below 15 K in order to enable complete renal clearance of the biocompatible PEG building blocks upon GMP degradation. The PEG-ester linkage used to make the PEG diacrylates can be tuned to provide a 20-fold change in hydrolysis kinetics using various diglycolate and succinate linkers. A second degradation strategy, utilizing PLA-PEG-PLA macromers to form hydrogels is used. The hydrolytically unstable polylactic acid ("PLA") segments on the ends of PEG chains enhance and determine degradation rates.

However, any of the sizes disclosed by U.S. Patent Appl. Pub. No. 2011/0268803 are suitable for use with the present invention.

The GMP polymers disclosed by U.S. Patent Appl. Pub. No. 2011/0268803 may be formed into gels by a free radical polymerization process. The GMP polymers may be formed into gels by a mannich linking reaction. The GMP polymers may be formed into gels by a process of hydrophobic association. The GMP polymers may be formed into gels by a cation mediated complex formation process. The GMP polymers may be formed into gels by an ester, amide, or disulfide crosslink between at least a portion of the polymers. The GMP polymers may be formed into gels by crosslink cinnamoyl groups.

The disclosed GMP polymers may include functionalized PEG polymers having a molecular weight from 200 to 200,000 g/mole. The GMP polymers may include functionalized PEG polymers with a molecular weight having any specific integer value in the range from 200 to 200,000 g/mole. The GMP polymers may include functionalized PEG polymers having a molecular weight in a range between and including any two specific integer values in the range from 200 to 200,000 g/mole. The GMP polymers may include functionalized PEG polymer having a molecular weight of any value in a range between and including any two integer values from 200 to 200,000 g/mole.

U.S. Patent Appl. Pub. No. 2011/0268803 discloses that the GMP polymers may include functionalized dextran polymers having a molecular weight from 200 to 100,000 g/mole. The GMP polymers may include functionalized dextran polymers with a molecular weight having any specific integer value in the range from 200 to 100,000 g/mole. The GMP polymers may include functionalized dextran polymers with a molecular weight in a range between and including any two specific integer values in the range from 200 to 100,000 g/mole. The GMP polymers may include functionalized dextran polymers having a molecular weight of any value in a range between and including any two integer values from 200 to 200,000 g/mole.

The GMP polymers are also disclosed that include functionalized polyvinyl pyrrolidone polymers or copolymers having a molecular weight from 200 to 100,000 g/mole. The GMP polymers may include functionalized polyvinyl pyrrolidone polymers or copolymers with a molecular weight having any specific integer value in the range from 200 to 100,000 g/mole. The GMP polymers may include functionalized polyvinyl pyrrolidone polymers or copolymers with a molecular weight in a range between and including any two specific integer values in the range from 200 to 100,000 g/mole. The GMP polymers may include functionalized polyvinyl pyrrolidone polymers having a molecular weight of any value in a range between and including any two integer values from 200 to 200,000 g/mole. The GMP polymers may include polymers formed from PLA-PEG-PLA macromers.

A further embodiment of the present invention is NPs and GMPs that enhance the proapoptotic effect of chemotherapeutic agents, such as camptothecin (CPT). Actively targeted NPs specifically deliver chemotherapeutic agents and chemopotentiators such as alpha-lipoic acid (ALA) to lung cancer cells to exploit synergy in tumor cell apoptosis induced by these two chemotherapeutic agents. By using the present invention with an appropriate chemopotentiator, the total dose of chemotherapeutic agents and GMPs will fall within the tolerable range for human patients and also be within the range of the currently approved macroaggregate ("MAA") products. Therapeutic targeting of the lung with therapeutic agents delivered by NPs within GMPs is also disclosed by U.S. Patent Appl. Pub. No. 2011/0268803.

As mentioned, a lung-specific delivery system may employ both passive and active targeting to intravenously deliver anti-cancer drugs to tumor cells. The first layer of the delivery system is a GMP designed to take advantage of the venous lung filtration pathway and passively accumulate in the lungs after intravenous injection into the body. The GMP may be composed of crosslinked, functionalized biocompatible polymers including but not limited to poly(2-hydroxyethyl methacrylate), dextrans, polyphosphates, poly(lactides), poly(glycolides) and polyethylene glycol (PEG) based polymers. Degradable linkages between the gel crosslinks can be incorporated to control the release rate of the NPs. The degradable linkages can include but are not limited to esters, succinates and diglycolates. The size of the GMPs may vary depending on the gel composition, but may be in the micron range.

In an embodiment, the GMPs have a size in the range from 1 to 100 µm. As a non-limiting example, the GMPs may have a size in the range between and including 6 µm and 7 µm. As another non-limiting example, the GMPs may have a size in the range between and including 6 µm and 20 µm. The deformability of the particles may be considered when choosing the size of the GMPs. In an embodiment, the GMPs are biocompatibile and safe.

A second layer of a delivery system may include one or more types of nanoparticles (NP) embedded in the GMP. In an embodiment, the second layer of the delivery system includes two types of NPs embedded in the GMP.

In an embodiment, the release rate of the NPs from the GMPs into the tumor and the release rate of the anti-cancer drug from the NPs can be tuned to achieve a desired effect. The GMP mesh size and degradation rate may control the release of the NPs.

As disclosed by U.S. Patent Appl. Pub. No. 2011/0268803, to produce GMPs on a commercial scale, emulsification techniques can be employed to make GMPs loaded with NPs. To create an emulsion, the aqueous soluble polymer with degradable linkages, NPs, crosslinking initiator and solvent are mixed and then introduced into a hydrophobic fluid phase. The aqueous solvent will form the discontinuous phase, while the hydrophobic fluid will form the continuous phase of the emulsion. The energy input controls the size of the droplets in the emulsion and hence the size of the GMPs. Once the emulsion is made, the droplets are crosslinked to create the GMPs. An effect of adding NPs to the aqueous phase, which will be polymerized to form the GMP, may be to increase the fluid phase viscosity and therefore increase emulsion drop size. The drop size may approximately correspond to the drop size that would be generated from a fluid with the continuous viscosity equal to that of the dispersion.

In an embodiment, the droplets of aqueous phase containing the polymer, drugs, and NPs can be produced by emulsification processes that are widely known by those in the art.

The droplets in the emulsion phase can be gelled using a variety of chemistries. These include but are not limited to free radical polymerization, mannich (i.e., thio-vinyl) reactions, hydrophobic association, metal ion mediated complexation, amide formation reactions, ester formation reactions, and azide alkyne Huisgen cycloaddition.

The radical reactions can be initiated with a variety of methods including but not limited to using UV light and photoinitiators, temperature, or redox initiation.

As disclosed by U.S. Patent Appl. Pub. No. 2011/0268803, the NPs may include PEG protective coatings. The plurality of NPs may be associated with the GMP by any physical combination. The plurality of NPs may be associated with the GMP by being mixed with the material of the GMP The plurality of NPs may be associated with the GMP by being loaded in the microparticle. The plurality of NPs may be associated with the GMP on the surface of the microparticle. The plurality of NPs may be associated with the GMP by being chemically linked to the GMP. The chemical linkage may be covalent. The chemical linkage may be degradable. The degradable linkages between a NP and material of a GMP can be but are not limited to ester degradable linkages, ketal degradable linkages, acetal degradable linkages, enzymatically degradable linkages, linkages degraded by reducing or oxidizing reactions and degradable orthoester linkages. The degradable linkages between a NPs and GMP can be all of one kind or more than one kind. The more than one kind can be selected from the preceding list of degradable linkages.

As disclosed by U.S. Patent Appl. Pub. No. 2011/0268803, hydrophobic drugs such as CPT can be loaded into NPs and their release controlled using Flash Nanoprecipitation ("FNP"). Applicants have developed a powerful technique using block-copolymer-directed assembly to prepare NPs from hydrophobic drugs at high loadings with narrow size distributions over the size range of 40-500 nm. Hydrophobic drugs and amphiphilic block copolymers were initially dissolved in a water-miscible organic solvent (THF, methanol, or DMSO). The solvent quality is then rapidly reduced by micromixing against water to produce supersaturations as high as 1000 that drive rapid precipitation of all hydrophobic components, i.e., the drug and the hydrophobic block of copolymer. Specifically, the process depends upon the (1) time to attain homogeneous mixing ($\tau_{mix}$), (2) time of solute nucleation and growth ($\tau_{ng}$), and (3) time of block copolymer self assembly ($\tau_{sa}$).

Figure 8:
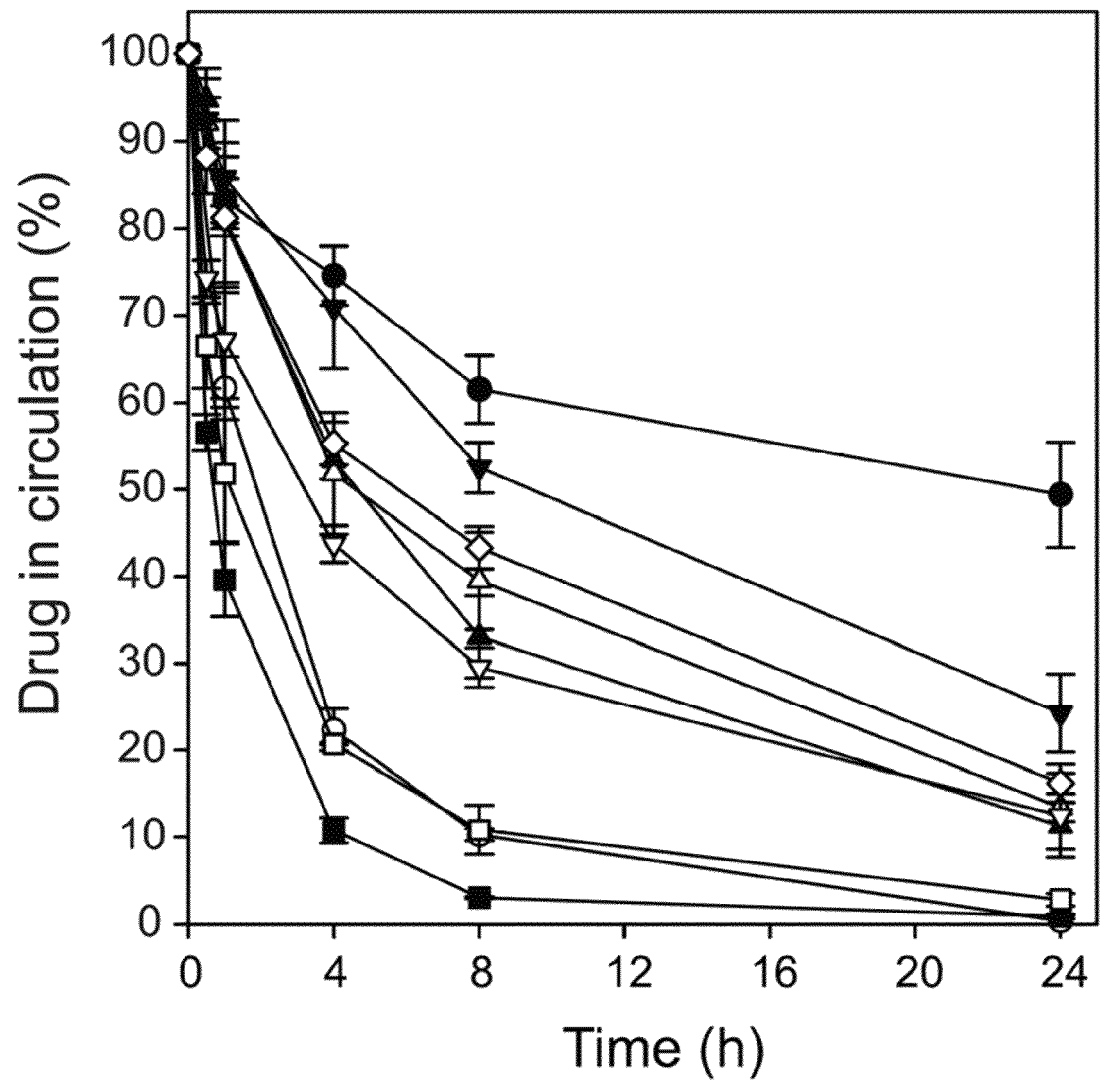
FIG. 8 illustrates Paclitaxel release from 70 nm NPs in Foxn1$^{nu}$ mice.

In the kinetically controlled assembly regimes at high super-saturations, NPs grow by diffusion-limited aggregation and incorporate the components stoichiometrically. Complex mixtures of multiple drugs, fluorophores, $Au^0$ colloids for X-ray imaging, and magnetic colloids for MRI imaging can be prepared. NP drug release kinetics are controlled using a novel prodrug conjugation strategy. For example, paclitaxel, a chemotherapeutic agent, was conjugated to a hydrophobic "anchor" molecule to retain it in the NP core until the hydrolytically unstable ester, ketal or orthoester is cleaved. By tuning the hydrolysis kinetics of the linker, paclitaxel release kinetics ($t_{1/2}$) can be tuned from 1 to 24 hours as shown in FIG. 8 for 70 nm NPs after IV tail injection in Foxn1 $^{nu}$ mice. This demonstrates that FNP enables the formation of NPs that can incorporate both chemotherapeutic agents and chemopotentiators into the same NP. The release kinetics of the actives can be tuned by selecting appropriate hydrophobic "anchors" and sacrificial conjugating linkages.

As disclosed by U.S. Patent Appl. Pub. No. 2011/0268803, NP diffusion out of hydrogel matrices such as GMPs can also be finely tuned. The active targeting aspect of the present invention relies on NPs that are imbedded into the GMP matrix. The diffusion of NPs through polymeric gels, such as GMPs, depends upon (1) the size of the diffusing species relative to the mesh size of the gel, (2) the fractal dimension of the diffusing species, and (3) and the diffusion distance, which, for the present invention, is the size of the GMP. NP diffusion out of the GMP matrix was predicted from Applicants' earlier measurements and the optimized GMP gel polymer concentration described above. Tests of the predictions are conducted on PEG diacrylate gels, which do not show degradation over a 7-day period. Fluorescence measurements of NP release from GMPs can then be conducted.

In a certain embodiment, the active targeting of the present invention is performed by functionalizing the surface of the NPs with specific targeting ligands. Copy number and density of active targeting ligands can be precisely controlled on the surface of NPs. NPs were produced with PEG protective coatings where the ends of the PEGs are functionalized for targeting. The ratio of neutral PEG to functionalized PEG is easily controlled by the FNP process to control targeting ligand concentration. The reactivity of the NP surface was linearly proportional to the fraction of maleimide in the PEG brush and the coupling of. Bovine Serum Albumin ("BSA") and luteinizing hormone-releasing hormone ("LHRH") peptides to the NPs for targeting has been demonstrated, notably in U.S. Patent Application Nos. 2005/0043215 and 2008/0280813, the disclosure of both are incorporated herein.

One is able to create extremely dense ligand concentrations on NP surfaces as well as controlling the mobility of the ligand by changing the structure of the linker. For example, for 30 nm NPs the number of PEG groups was about 600. The maximum BSA density on the NPs was 69 BSA/NP. With the hydrodynamic radius of BSA of 3.7 nm, a maximum of 66 BSA molecules would fit on the surface of a 30 nm sphere. To avoid denaturation during solvent precipitation, sensitive molecules require coupling after formation of the NPs. Applicants have demonstrated this with LHRH ligand NP targeting to MS578T breast cancer cells in vitro as detailed in the above published applications. Thus, using FNP, NPs are created with cancer cell targeting functionality using peptide and non-peptide ligands.

As previously noted, the present invention is not limited to lung-specific delivery system that employs both passive and active targeting to intravenously deliver anti-cancer drugs to lung tumor cells. The NPs of the present invention can be loaded with appropriate chemotherapeutic agents and chemopotentiators and surface-functionalized with ligands that target other types of cancer cells. Those outside the lung will not benefit from the passive targeting method of the present invention.

One embodiment of suitable targeting ligands is antibodies. Examples of suitable antibodies include, but are not limited to abciximab, basiliximab, cetuximab, infliximab, rituximab, trastuzumab etc. Other embodiments of suitable targeting ligands include, but are not limited to, peptides, hormones, vitamins, growth factors, carbohydrates. Examples include, but are not limited to, folic acid, cyclic or linear peptides with RGD motif, peptides with EGF motif, DV3 peptide, Lyp peptide, peptide binding domain of IGFBP3, fMLF, luteinizing hormone releasing hormone (LHRH), transferrin, β-galactoside or N-acetylgalactosamine, mannose etc.

An embodiment of the present invention utilizes the synergy between CPT and ALA to more effectively treat NSCLC thus reducing the (1) CPT dose and (2) number of GMPs required for treatment. Significantly, CPT is a drug candidate that failed in clinical development because of toxicity, poor oral bioavailability, poor solubility in biological fluids, inappropriate pharmaco-kinetics, and lack of efficacy within a tolerable dose range. The present invention thus makes possible the safe and effective delivery of CPT and other chemotherapeutic drug candidates with similar shortcomings for the treatment of cancer. Minimizing the dose of CPT/ALA-GMPs required for IV injection reduces the potential for lung toxicity due to the particles and the side effects of CPT. This is accomplished by performing a battery of in vitro and in vivo studies described below to assess chemopotentiation resulting in the calculation of the Dose Reduction Index ("DRI"). Unformulated CPT and ALA is studied in vitro to determine the Combination Index ("CI") and DRI. CPT and ALA are then loaded into NPs at their optimal CI. In a further embodiment, because CXCR4 is over-expressed in lung cancer, the surface of NPs are functionalized with DV3, a peptidic ligand that is known to interact with CXCR4. DV3 and a backup targeting ligand, folate, can be attached to the block copolymer prior to assembly using click chemistry. Utilizing the method described above, DV3-NP copy number and surface density is optimized for A549 cell uptake. DV3-NPs are loaded into GMPs and release testing is performed as described below. In vivo studies are then performed in an orthotopic mouse model.

Since most chemotherapeutic approaches ultimately elicit their effects via apoptosis, manipulation at the level of apoptosis control is highly attractive. Chemopotentiation fulfills two important functions: (1) it selectively sensitizes cancer cells to chemotherapy without affecting normal cells and (2) increases apoptotic drive. ALA refers to a racemic mixture of the R- and s-enantiomers. Although in vitro animal and human studies have used both racemic and R-ALA, only the r-enantiomer occurs in nature and is thought to be more bioactive. The R-enantiomer is available as a free acid and as sodium (Na-RALA) and potassium (K-RALA) salts. Although ALA has exhibited anti-cancer activity, which is thought to be due to stimulation of oxidative phosphorylation (OXPHOS), for the purposes of the current embodiment of the present invention R-ALA is used. The rationale is four-fold: (1) the r-enantiomer is more potent at stimulating mitochondrial OXPHOS, (2) the s-enantiomer can act as an anti-metabolite, blocking the activity and chemical reduction of r-ALA99, (3) the r-enantiomer is reduced to difiydrolipoic acid (DHLA) 24 times faster than the s-enantiomer and (4) DHLA is at least, if not more, cytotoxic towards cancer cells. Utilization of this embodiment of the present invention results in increased ALA potency, thus resulting in lower required doses. In addition ALA induces caspase activation for about 24 hours, so large doses will not be needed in order to maintain optimal synergy conditions for the week long treatment regimen of this embodiment of the present invention.

In certain embodiments, a drug may be loaded in the GMP. A drug may be loaded onto a GMP similar to the means by which it is loaded onto a nanoparticle, i.e., by physical admixture or covalent attachment. A targeting ligand may also be covalently attached to the GMP surface. A chemopotentiator may be associated loaded onto a GMP similar to the means by which it is loaded onto a nanoparticle, i.e., by physical admixture or covalent attachment.

While the preceding discusses the use of CPT as the chemotherapeutic agent in the present invention, it should be understood that the active targeting disclosed herein can be used with a variety of chemotherapeutic agents to treat cancers other than lung cancers. Chemotherapy and therapeutic anticancer agents which can be used include, cytotoxic agents such as Taxol, Cytochalasin B, Gramicidin D, Ethidium Bromide, Emetine, Mitomycin, Etoposide, Tenoposide, Vincristine, Vinblastine, Colchicin, Doxorubicin, Daunorubicin, Mitoxantrone, Mithramycin, Actinomycin D, 1-Dehydrotestosterone, Glucocorticoids, Procaine, Tetracaine, Lidocaine, Propranolol, and Puromycin and analogs or homologs thereof.

Therapeutic agents include, but are not limited to, antimetabolites (e.g., Methotrexate, 6-Mercaptopurine, 6-Thioguanine, Cytarabine, 5-Fluorouracil, Decarbazine), alkylating agents (e.g., Mechlorethamine, Thiotepa, Chlorambucil, Melphalan, Carmustine (BCNU), Lomustine (CCNU), Cyclophosphamide, Busulfan, Dibromomannitol, Streptozotocin, Mitomycin C, Cis-Dichlorodiamine Platinum (II) (DDP), Cisplatin), anthracyclines (e.g., Daunorubicin (formerly Daunomycin) and Doxorubicin), antibiotics (e.g., Dactinomycin (formerly Actinomycin), Bleomycin, Mithramycin, and Anthramycin (AMC)), anti-mitotic agents (e.g., Vincristine and Vinblastine) and selective apoptotic agents such as APTOSYN® (Exisulind), PANZEM™ (2-methoxyestradiol), and VELCADE® (bortezomib), a proteasome inhibitor.

Anticancer agents for the treatment of ovarian cancer can include one or more of the following: Etoposide, Melphalan, Cisplatin, Carboplatin, CPT, Paclitaxel, Anthracylines (e.g., Doxorubicin), Hexamethylamine (Altretamine), Progestins (e.g., Medroxyprogesterone acetate, Megestrole acetate), 5-Fluorouracil plus Leucovorin (to counteract folic acid antagonists), Ifosfamide, or Topotecan.

Anticancer agents for the treatment of breast cancer include Doxorubicin, PANZEM™. (2-methoxyestradiol), Paclitaxel, Methotrexate, 5-Fluorouracil, Docetaxel, Thiotepa, Cisplatin, Estrogen receptor modulators such as Tamoxifen and Toremifene, Estrogens (e.g., diethylstilbestrol), Androgens (e.g., fluoxymesterone), Gonadotropin-Releasing Hormone (GnRH), Anastrozole, Aromatase inhibitors (antineoplastics), Vinorelbine tartrate, Gemcitabine hydrochloride, Progestins (e.g. Medroxyprogesterone acetate, Megestrole acetate), Trastuzumab (HERCEPTIN®) and Cyclophosphamide.

Anticancer agents for colorectal cancer treatment can include Oxaliplatin, 5-Fluorouracil, or Leucovorin.

Exemplary anticancer agents for the treatment of prostate cancer can include anti-androgens (e.g., Flutamide, Nilutamide, Bicalutamide, Cyproterone, Megestrol) and the Leuteinizing Hormone-Releasing Hormone analogues (e.g., Buserelin, Goserelin, Leuprolide).

Anticancer agents for liver cancer treatment can include 5-Fluorouracil, Leucovorin, RaltitreXed, Mitomycin C, and CPT-1.

Other anticancer agents for the treatment of lung cancer can include Paclitaxel, Carboplatin, Vinorelbine tartrate, Gemcitabine hydrochloride, Etoposide, Doxorubicin, Ifosfamide, Docetaxel, Cyclophosphamide, Methotrexate, Lomustine (CCNU), Topotecan hydrochloride, and Cisplatin. These agents can be used in active targeting alone, passive targeting alone, or in the embodiment of the invention combining active and passive targeting.

Examples of other anticancer agents suitable for use with the present invention include Abarelix, Aldesleukin, Alemtuzumab, Alitretinoin, Allopurinol, Altretamine, Amifostine, arsenic trioxide, asparaginase, bevacuzimab, bleomycin, bortezomib, capecitabine, carmustine, celecoxib, cetuximab, cladribine, clofarabine, dexrazoxane; epirubicin, Epoetin alfa, Erlotinib, Estramustine, etoposide phosphate, VP-16, exemestane, Filgrastim, Floxuridine, Fludarabine, fulvestrant, gefitinib, gemtuzumab, histrelin acetate, hydroxyurea, idarubicin, imatinib mesylate, interferon alfa 2a, irinotecan, lenalidomide, letrozole, Levamisole, nitrogen mustard, L-PAM, mesna, methoxsalen, mitotane, nelarabine, Nofetumomab, Oprelvekin, Palifermin, Pamidronate, Pegademase, pemetrexed disodium, pentostatin, pipobroman, plicamycin, porfimer sodium, procarbazine, quinacrine, Rasburicase, Rituximab, Sargramostim, Sorafenib, sunitinib maleate, temozolomide, VM-26, testolactone, Tositumomab, Uracil Mustard, Zoledronate and zoledronic acid.

Additionally, a variety of chemopotentiators can serve as an alternative to ALA. These include, but are not limited to metabolism-modifying agents such as lipoic acid, lipoic acid analogues, sodium-r-alpha lipoate, dichloroacetate (DCA), carnosine, flavin mononucleotide (FMN), flavin adenine dinucleotide (FAD), coenzyme Q10 (ubiquinone), idebenone, mitochondrial uncouplers (e.g. aspirin, indomethacin, nimesulide, meloxicam, diclofenac, piroxicam, valinomycin, nigericin); multi-functional agents such as methylsulfonylmethane (MSM), phytochemicals (e.g. monophenols, flavonoids, phenolic acids, hydroxycinnamic acids, lignans, tyrosol esters, carotenoids, monoterpenes, saponins, lipids, betalains, organosulfides, indoles, glucosinolates/sulfur compounds, organic acids), vitamins (e.g. tocohperols, tocotrienols, vitamin D, vitamin D analogues) and mineral compounds (e.g. potassium iodide, iodine, selenium, zinc); and anti-inflammatory agents such as non-steroidal anti-inflammatory drugs (e.g. aspirin, ibuprofen, naproxen, indomethacin, celecoxib, sulindac, diclofenac), fatty acids (e.g. eicosapentaenoic acid, docosahexaenoic acid, alpha linolenic acid, gamma linolenic acid, ricinoleic acid), and phytochemicals (e.g. curcumin, resveratrol, quercetin, lutein, and lycopene).

Figures 14A, 14B:
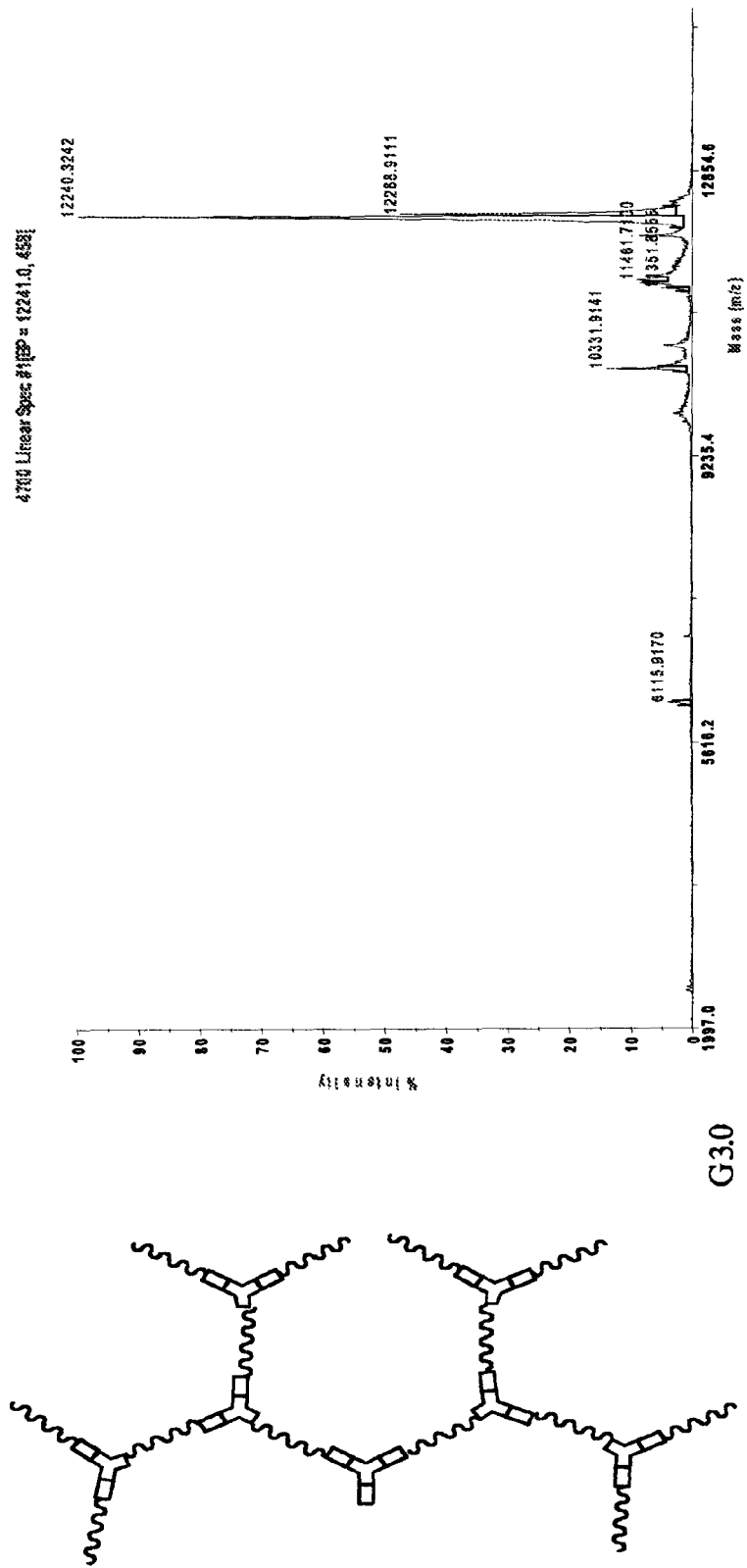
FIG. 14 (a) shows a structure diagram of PEG-based dendrimer (generation 3.0, G3).

As an alternative to the use of DV3-NPs in the treatment of lung cancer, DV3 can be replaced with recently identified peptidic/peptoid CXCR4 antagonists (see e.g., T. Narumi et al., Org Biomol Chem. 2010 Feb 7;8(3):616-21). Phage display will be used to isolate/characterize unique peptidic CXCR4 antagonists. Additionally, a novel PEGtide dendrimer as shown in FIG. 14(a) can be used as a nanocarrier. An embodiment of this PEGtide dendrimer is represented by Formula 1:

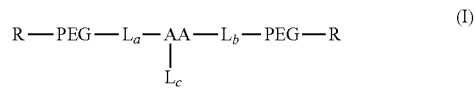

wherein R is:

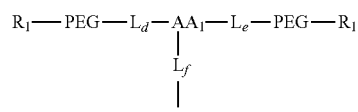

$R_1$ is:

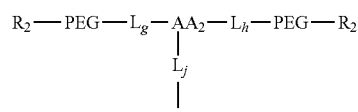

$R_2$ is:

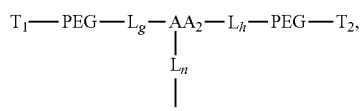

PEG is linear or branched poly(ethylene glycol);

AA, $AA_1$, $AA_2$, and $AA_3$ are each independently lysine or ornithine;

$L_a$, $L_b$, $L_c$, $L_d$, $L_e$, $L_f$, $L_g$, $L_h$, $L_j$, $L_k$, $L_m$, and $L_n$ are each independently 0-8 amino acids long and selected from alanine, glycine, val-ine, leucine, isoleucine, statine, phenylglycine, phenylalanine, cysteine, penicillamine, homocysteine, arginine, histidine, norvaline, norleucine, 2-fluorophenylalanine, 3-fluorophenylalanine, 4-fluorophenylalanine, β-cyclohexyl-alanine, 2-aminobutyric acid, 4-aminobutyric acid, 6-aminobutyric acid and α-amino-butyric acid;

$T_1$ and $T_2$ are free, protected amino groups or a therapeutic agent. This novel PEGtide dendrimer is described in more detail in the patent application titled "POLYETHYLENE GLYCOL-BASED DENDRONS" filed on the same day the present patent application, the disclosure of which is incorporated herein.

Further, additional alternative targeting ligands include, but are not limited to, peptides, hormones, vitamins, growth factors, carbohydrates. Examples include, but not limited to, folic acid, cyclic or linear peptides with RGD motif, peptides with EGF motif, Lyp peptide, peptide binding domain of IGFBP3, fMLF, luteinizing hormone releasing hormone (LHRH), transferrin, β-galactoside or N-acetylgalactosamine, mannose etc.

A further embodiment of the present invention is CXCR4/7-targeted NPs and GMPs that reduce the occurrence of metastasis. Representative active targeting approaches of this embodiment include: (1) direct CXCR4/7 receptor binding and (2) inhibition of downstream pro-metastatic signaling factors NF-κB, ERK and/or MMP-9.

Figure 13:
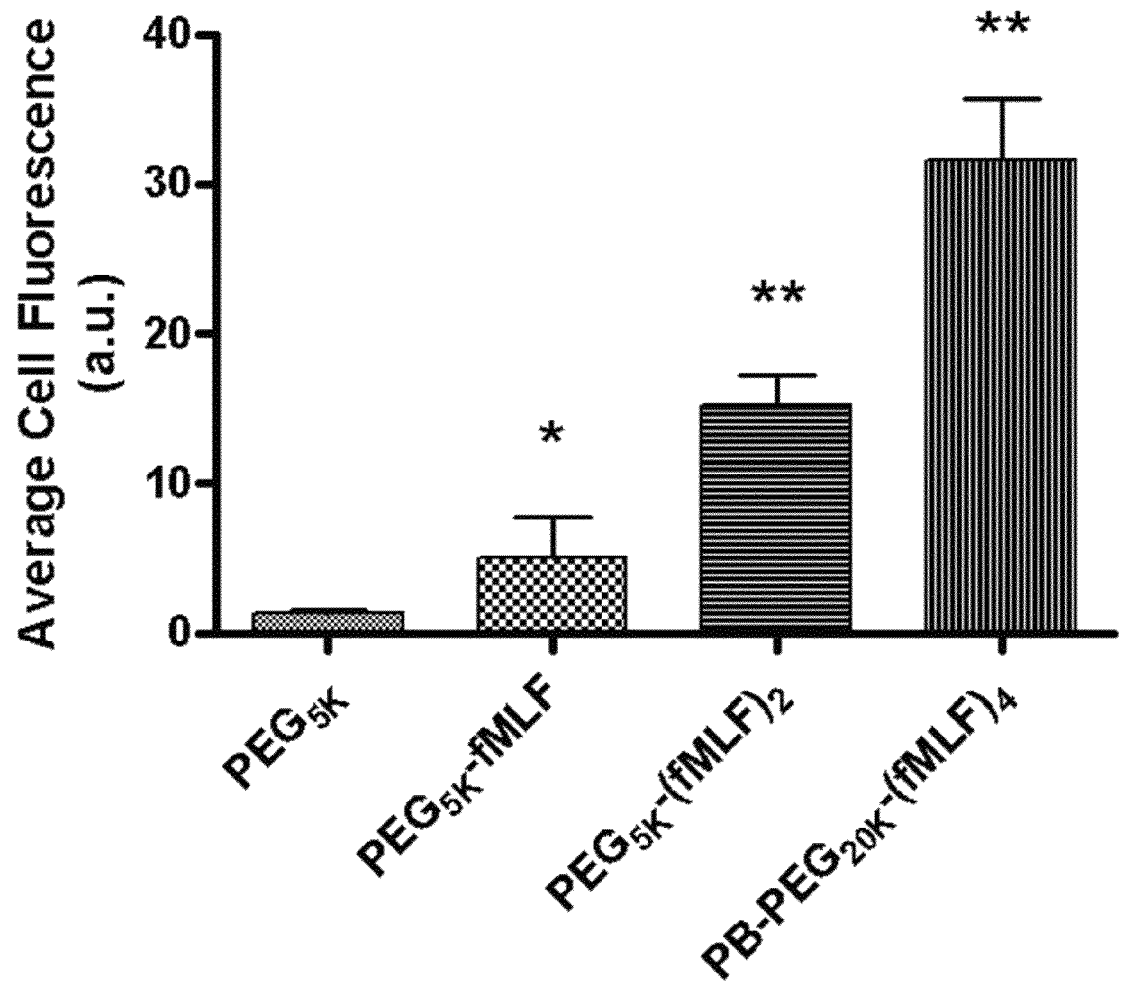
FIG. 13 shows the uptake of PEG-fMLF nanocarriers in mouse peritoneal macrophages at 37'C after 4h of incubation. Means±SD for three experiments are shown for each value. (*Statistically significant difference between the control PEG5K and PEG-fMLF nanocarriers. P<0.05, **P<0.01).

Applicants have determined that nanocarriers with multiple ligand copies improve cell targeting and control cell disposition. The nanocarrier may be internalized or remain on the cell surface depending on the size of the nanocarrier and the number and spacing of targeting ligands as well as flexibility of the ligand linker. As seen in FIG. 13, the non-functionalized nanocarrier is not taken up into peritoneal macrophages in vim. The addition of one copy of the ligand (fMLF) only slightly improves interactions with the formyl peptide receptor. However, as copy number increase even large nanocarriers are taken up in vivo nearly 20× more than non-functionalized nanocarriers. Additionally, nanocarriers can be engineered to tightly bind and remain on cell surfaces. Thus, controlling ligand copy number, spacing and the flexibility of the ligand linker enable the tuning of NP cellular disposition kinetics.

NSCLC is characterized by a specific metastatic pattern metastasizing to regional lymph nodes, liver, adrenal glands, contralateral lung, brain, and bone marrow. A battery of in vitro and in vivo studies described below were used to assess the effectiveness of interfering with the CXCR4/7-CXCL12 chemokine pathway to reduce the formation of metastatic lesions. First, DV3 surface functionalized NPs are designed and evaluated for the ability to bind to CXCR4/7 and inhibit the pro-metastatic signaling pathway. Second, NPs containing ALA or doxycycline (DOXY) are prepared and evaluated for their ability to inhibit the pro-metastatic signaling pathway. Both agents are hydrophobic and they are readily encapsulated into the NPs using the FNP method. The DV3-NPs are then evaluated for binding to CXCR4/7 as well as cellular disposition (surface localization versus internalization) in a variety of cell lines. DV3-NPs that remain tightly bound to the cell surface, ALA-NPs and DOXY-NPs are then evaluated in a variety of in vitro metastasis assays using the combination algorithm described above. The Dose Reduction Index and Combination Index (CI) are calculated as previously described. The optimal DV3-NPs, ALA-NPs, and DOXY-NPs are then evaluated in an orthotopic mouse model as described above for evidence of metastasis.

The expression of CXCR4 is associated with distant NSCLC metastases and shorter survival times. Recently, CXCR7 was also linked to NSCLC metastasis. Activation of CXCR4 or CXCR7 induces NSCLC cell migration and adhesion to stromal cells that secrete CXCL12, which in turn provides growth and drug resistance signals to the tumor cells. CXCR4 antagonists disrupt CXCR4-mediated cell-adhesion to stromal cells as well as sensitize cells to cytotoxic drugs and thereby antagonize cell adhesion-mediated drug resistance. Specifically, activation of CXCR4 by CXCL12 triggers downstream signaling cascades that upregulate NF-κB, ERK and MMP-9. Increased MMP activity of tumor cells indicates a higher invasive and metastatic potential.

Interfering with CXCR4-CXCL12 interactions and downstream signaling: DV3 was selected as a targeting ligand because it binds to CXCR4. In addition to disrupting the CXCR4/CXCL12 chemokine pathway, blocking downstream signaling factors such as NF-κB, ERK and MMP-9 provide a viable approach. ALA has been shown to inhibit NF-κB, ERK, and MMP-9. Doxycycline, which inhibits cancer cell proliferation, is one of the more potent MMP inhibitors of the tetracycline family. The present invention will allow one to sustain levels of these agents in or near NSCLC cells representing an effective method to treat NSCLC.

Three combination studies are performed to assess the in vivo performance of this embodiment of the present invention: (1) CPT+DV3-NPs, (2) CPT+ALA, and (3) CPT+DOXY. Negative controls include solvent only and non-treated animals. The optimal concentrations and CI's determined from the in vitro studies are investigated. In vivo studies follow the general design and analysis described above for the other embodiments of the present invention.

The delivery systems and methods herein may include a pharmaceutically acceptable salt, solvate or derivative of a drug or targeting agent. Pharmaceutically acceptable salts that may be included in embodiments herein can be found in Handbook of Pharmaceutical Salts: Properties, Selection, and Use, Stahl and Wermuth (Eds,), VHCA, Verlag Helvetica Chimica Acta (Zurich, Switzerland) and WILEY-VCR CWeinheim, Federal Republic of Germany); ISBN: 3906390-26-8, which is incorporated herein by reference as if fully set forth.

The delivery systems and methods herein may include pharmaceutically acceptable carriers, which may be selected from but are not limited to those in the following list: ion exchangers, alumina, aluminum stearate, lecithin, serum proteins, human serum albumin, buffer substances, phosphates, glycine, sorbic acid, potassium sorbate, partial glyceride mixtures of saturated vegetable fatty acids, water, salts or electrolytes, protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, waxes, polyethylene glycol, starch, lactose, dicalcium phosphate, microcrystalline cellulose, sucrose, talc, magnesium carbonate, kaolin, non-ionic surfactants, edible oils, physiological saline, bacteriostatic water, Cremophor ELTM (BASF, Parsippany, N.J.) and phosphate buffered saline (PBS).

The invention is described in greater detail by the following non-limiting examples.

EXAMPLES

Statistical Design and Analysis

Compusyn 3.01 (Combosyn Inc, Paramus, N.J.) is used to quantitatively analyze drug combination and dose-effect relationships. All data (e.g., dose-response of drug 1, drug 2, and drug 1+drug 2) is used to construct median-effect plots using $\log[fa/(1-fa)] = m\log D - m\log(ID50)$, where fa is the fraction of system affected by dose D, ID50 is median dose for tumor inhibition, and m is a Hill-type coefficient (m) signifying the sigmoidicity of the dose-effect curve. ID50 values of individual drug 1, drug 2, and combination drug 1+drug 2 as well as m can be obtained from the plots. For a selected effect (x%), doses of drug 1 (Dx1), drug 2 (Dx2) and drug 1+drug2 (Dx1+2) needed to produce this effect will be calculated using $Dx = ID50[fa/(1-fa)]1/m$. Dx1+2 will be further dissected into dose fractions of drug 1 [(D)1] and drug 2 [(D)2] by equations $(D)1 = Dx1+2 \times P/(P+Q)$ and $(D)2 = Dx1+2 \times Q/$ (P+Q), where P:Q is the molar ratio of drug 1 to drug 2. Combination index (CI): CI=(D)1/Dx1+(D)2/Dx2. CI<1, =1 and >1 represent synergistic, additive and antagonistic effects, respectively. Dose-reduction index (DRI): represents the fold reduction in drug dose at a given effect level compared to individual drug doses. DRI1=Dx1/(D)1.

Example 1

Figures 2A, 2B:
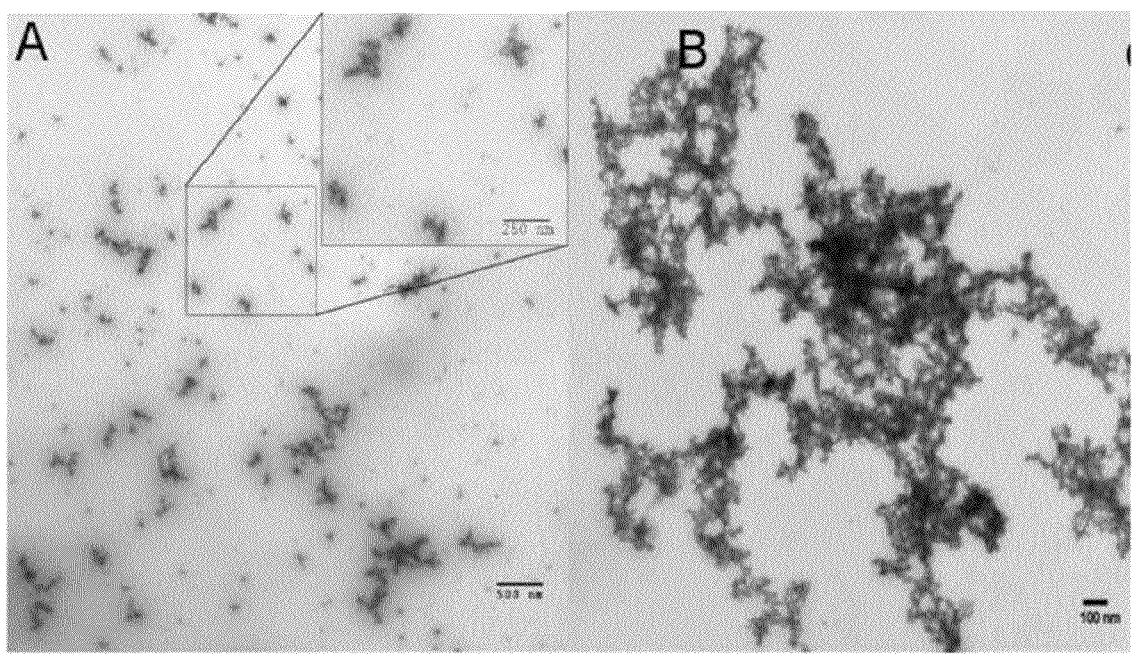
FIG. 2 shows TEM images of PEG nanogels (a) and micron-sized aggregated nanogel particles (ANPs) (b) that were negatively stained using aqueous solution of 0.5% uranyl acetate.

PEG nanogels (~20 nm) were prepared using a 20 kDa 8-arm PEG-SH nanocarrier crosslinked using a HVBS linker at various stoichiometries (1:1, 0.5:1, and 0.8:1). FIG. 2 shows typical TEM images of nanogels (Panel A) and ANPs in the low micron size range (Panel B) that were negatively stained using aqueous solution of 0.5% uranyl acetate. As the ANPs self-assemble, they take on a more flexible spider-like shape similar to that reported for the commercial MAA lung perfusion diagnostic MPs.

Figure 3:
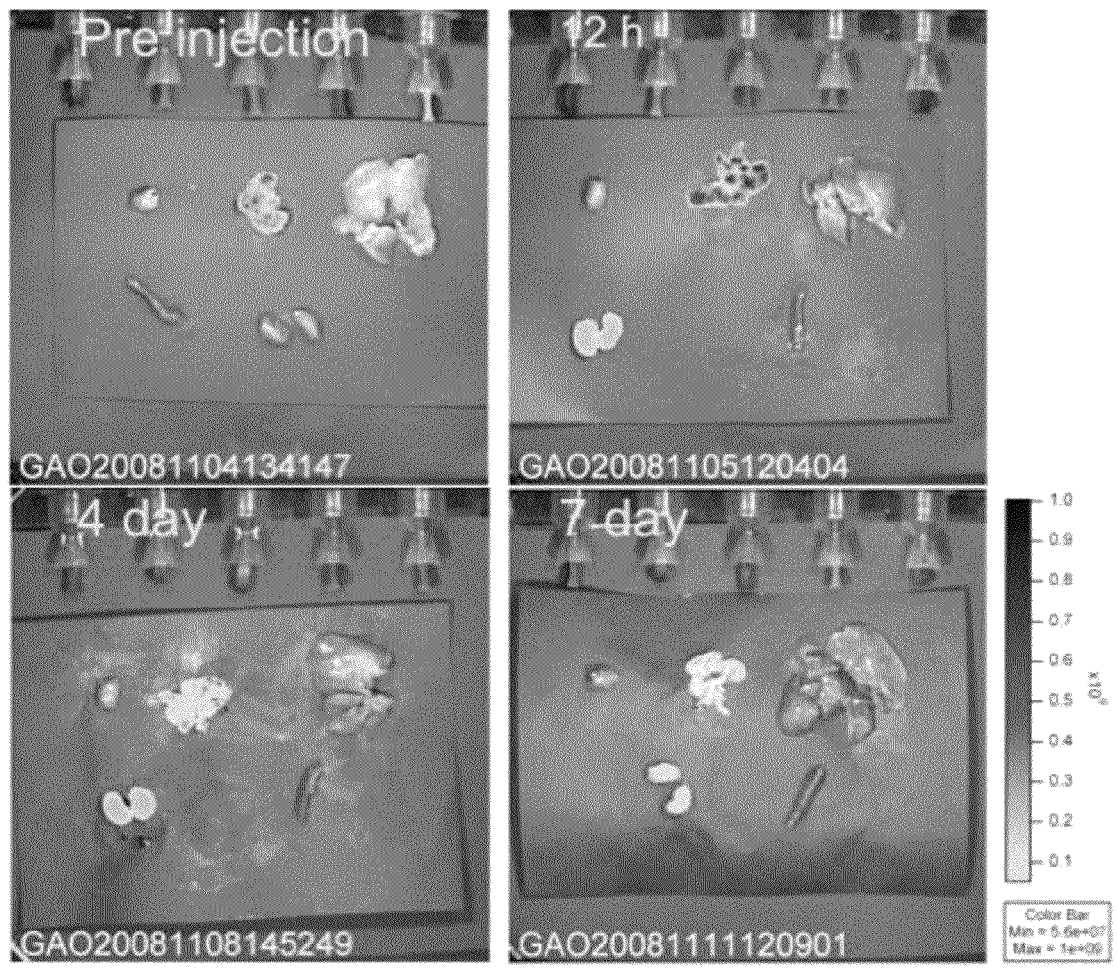
FIG. 3 shows ANP accumulation following the IV administration of 55 μm DYE-ANPs (16 mg/kg) via the tail vein to healthy rats.

Bio-distribution studies of ANPs covalently labeled with HiLyte750 dye ("DYE-ANPs") were performed. ANPs of three sizes were prepared (10-30, 30-50 and 50-60 μm). DYE-ANPs were administered (16 mg/kg) to male Sprague-Dawley rats by tail vein injection. Biodistribution of ANPs was determined using IVIS. Peak ANP accumulation was found to occur between 6-12 hr. ANPs were retained in the lungs in high concentrations for 4-5 days with detectable amounts through the 7 days of the study. Larger ANPs (50-60 μm) preferentially accumulated in the lung within 30 min with the majority remaining in the lung for more than 7 days (FIG. 3). Although smaller ANPs (10-30 μm) also accumulated in the lung with high efficiency, the overall residence time was approximately one week with a reduced signal after about 3-4 days. Intermediate results were observed for medium sized ANPs (30-50 μm). Toxicity was not observed at any of the doses administered. This investigation demonstrated that the lung targeting efficiency of all 3 sizes of ANPs studied was high (>95%) while lung retention varied according to size. Further, ANPs in the 30 μm range provide optimal lung retention.

Figure 6:
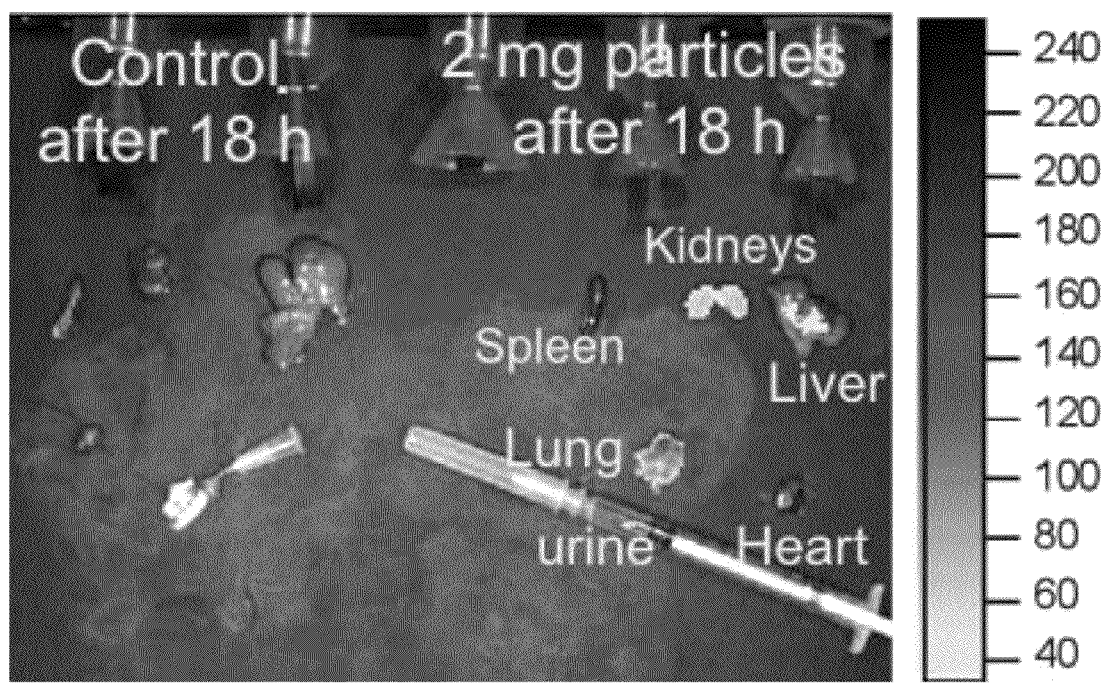
FIG. 6 shows lung accumulation of 25 μM ANPs in mice 18 h after IV injection of 1 mg of ANPs.

Bio-distribution studies of ANPs covalently labeled with HiLyte750 dye (DYE-ANPs) were performed to determine the species dependence of lung accumulation and retention. 200 μL PBS (control) or DYE-ANPs (Dose: 1 mg in 200 μL PBS, Particle size: 25 μm) were administered intravenously to BALB/C mice. Biodistribution of DYE-ANPs was determined using IVIS. DYE-ANPs were found to accumulate in the lung with the same pattern as rats (18 hour time point is shown in FIG. 6). These results are consistent with literature that there is not a major difference between species and their MP accumulation patterns in the lung.

Example 2

Preparation of GMPs by Microfluidics

Figure 7:
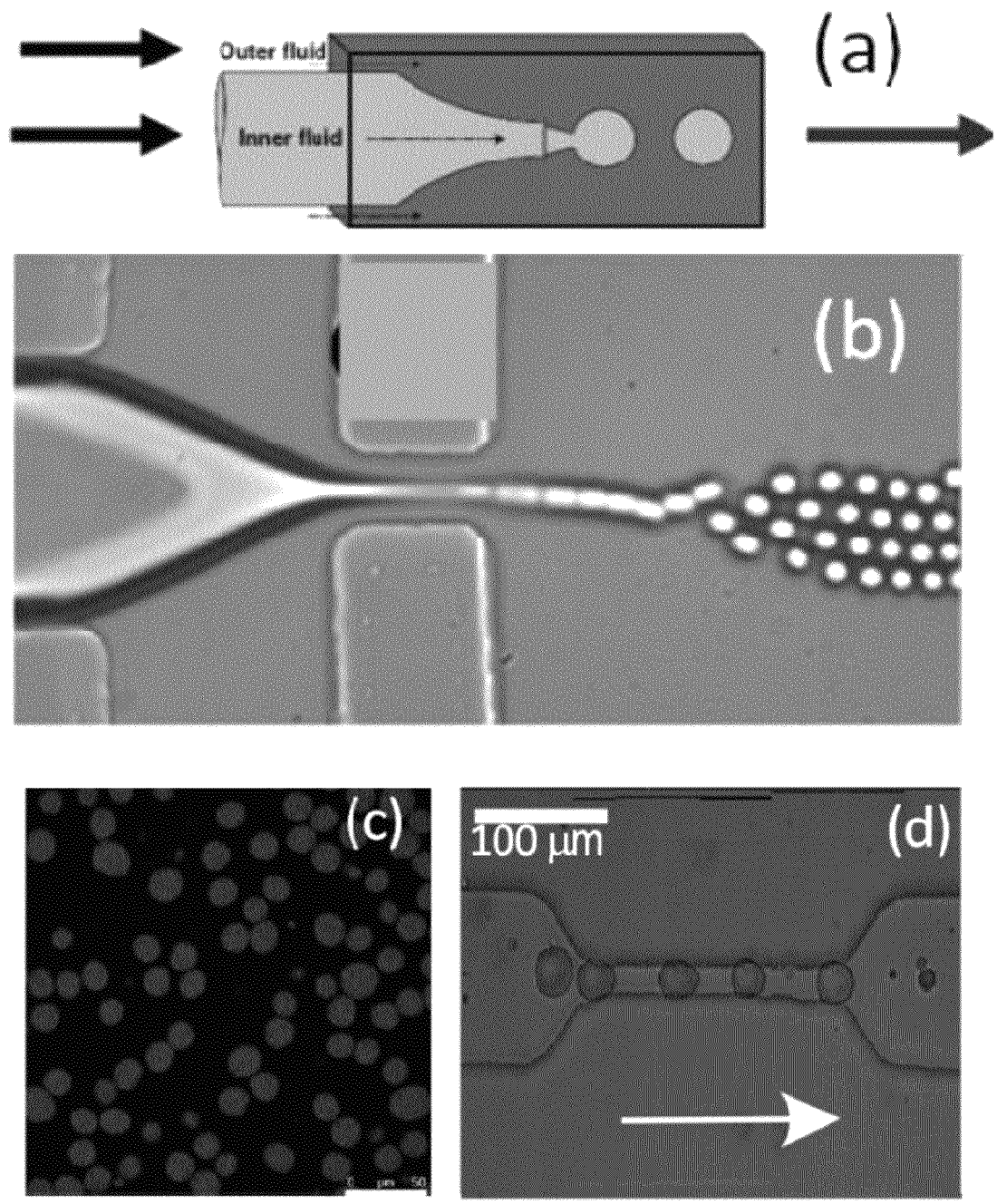
FIG. 7 displays (a) a schematic of flow focusing geometry where the outer sheath flow stretches and breaks the drops into a uniform size, (b) images of drop breakup for flow through a 43.5 μm orifice with a ratio of inner to outer flow rates of Qi/Qo=1/40, (c) PEG polymerized GMPs with an average size of 8 μm containing 100 nm NPs containing fluorescent dye showing the successful production of NPs encapsulated in GMPs, and (d) time-lapse image of PEG polymerized 25 μm GMPs being forced through a 20 μm contraction as a model of capture in the lung capillaries.

The sheath fluid consisted of PDMS (Dow Corning Corporation 749®fluid, Aldrich) containing about 2.0 weight percent initiator (2-Hydroxy-4'-(2-hydroxyethoxy)-2-methylpro-piophenone). For the gel phase, an aqueous solution of 75 percent volume PEG diacrylate macromer (Sartomer, SR259), 0.07 weight percent initiator and 2.0 weight percent SDS was used. 100 nm NPs containing red fluorescent dye (Ciba, Hostasol red) were incorporated (1 NA percent of NPs) to produce the brightly fluorescent about 10 μm droplets as shown in FIG. 7(*c*). The GMP gel phase encapsulates the NPs containing the fluorescent dye.

The microfluidic chips were prepared using standard methods of soft lithography. Prior to injection, the micro-fluidic chips were treated with octadecyltrichlorosilane ("OTS") to make the glass surface hydro-phobic. Flow rates of the oil and aqueous phases were adjusted to achieve a monodisperse sus-pension of water droplets with a diameter of about 10 μm suspended in the oil phase. Droplets were collected in three vials and the vials were exposed under a longwave UV lamp (Ultra-Violet Products Inc., Blak-Ray®) for different time (1, 3, and 9 minutes), which adjusts the degree of cross-linking and ultimately GMP softness (i.e., shear modulus G). The modulus is varied by changing: (1) the molecular weight of the PEG macromer where decreasing the molecular weight from 3000 to 200 will increase the modulus by 60 fold, (2) the macromer concentration, (3) the extent of reaction by varying the UV exposure time, and (4) the ratio of linear, four arm and 8 arm PEG macromers. The combined factors enable varying the modulus by at least three orders of magnitude.

A time-lapse photograph of a GMP entering a constriction is shown in FIG. 7(*d*). This provides a method of qualitatively assessing stiffness because one can make constrictions of sizes from 4-20 μm and visualize the entry or trapping of the GMPs in the constriction. The correspondence between in vitro to in vivo accumulation is then determined. Quantitative determination of GMP stiffness is made by measuring the modulus of gel slabs of the same composition as GMPs using an Anton Paar MCR500 rheometer in a parallel plate geometry. Using this technique, Applicants have demonstrated the production of uniform GMPs in the size range of about 6 to about 20 μm by microfluidics and the encapsulation of fluorescent 100 nm NPs in the GMP polymer network.

Example 3

Size and deformability are the two major determinants of MP passive lung accumulation and retention. To determine that a larger sized deformable GMP has the same lung targeting properties as a smaller rigid MP, at least four GMPs with wide ranging deformabilities using a microfluidic approach are produced. For each type of deformable GMP, a range of sizes are produced. Passive lung targeting is then assessed in normal mice for each GMP type in order to determine the optimal size for a fixed level of deformability. Toxicology and lung function are investigated for the optimally sized GMP at each level of deformability. GMP lung retention time is optimized by engineering the degradation rate of the GMP matrix. As GMPs spontaneously degrade, their size is reduced to a critical value allowing clearance from the lungs.

The rules learned about optimum GMP size and modulus are the basis for synthesizing PEG macromers with appropriate degradable ester and PLA linkages to tune both the GMP clearance rate from the lungs and the NP release kinetics from the degrading GMP.

An orthotopic NSCLC mouse model was used to facilitate the in vivo imaging component of the studies. Orthotopic mouse models are well documented with stage IV-like intrapulmonary and distal metastasis. Human A549 NSCLC cells were co-transfected with Katushka, a far-red fluorescent protein, and luciferase to facilitate tumor detection by in vivo/ex vivo imaging and microscopy. Transfected A549 (106 cells in 0.05 ml of 0.5 mg/ml Matrigel) cells were implanted through the thorax into the left lung parenchyma.

To assess lung toxicity and function, GMP was injected into CD-1 mice intravenously. Lung function was measured using a Scireq Flexivent at 1 and 7 days after injection. The mice were euthanized, and bronchoalveolar lavage ("BAL") fluid was collected and evaluated for biomarkers of lung injury, inflammation and oxidative stress. The lung was subjected to histologic scoring for severity of injury, morphologic/structural changes, and inflammation. The Scireq Flexivent provided information on respiratory system mechanics including total lung resistance, which equals central airway resistance plus peripheral lung resistance, and static compliance responses at baseline and in response to pharmacologic challenge.

Figure 5:
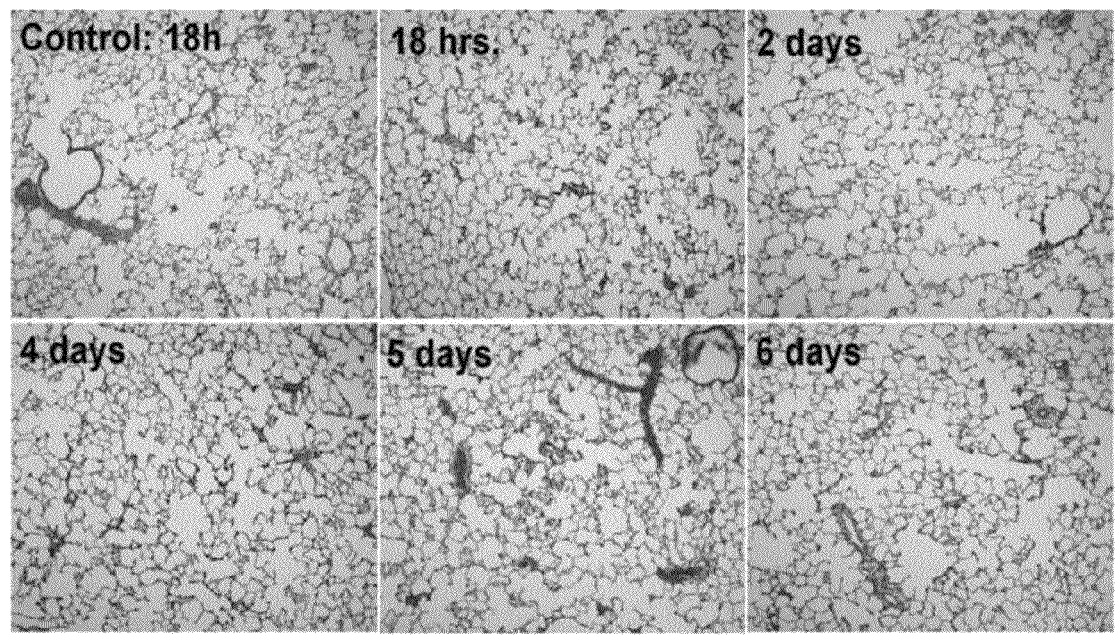
FIG. 5 shows lung histology following ANP (20 μm) injection. Lung samples were collected at 18 hours to 6 days post particle injection, embedded in paraffin and sections stained with H & E. (Magnification 100×)

Additionally, to determine the safety of an embodiment of the present invention, histologic sections of lungs from rats treated with ANPs were assessed for evidence of toxicity by utilizing confocal microscopy. FIG. 4 shows fluorescently labeled ANPs localized in pulmonary capillaries. No significant structural alterations were noted in the lung. In addition to these results, FIG. 5 shows lung samples that were collected at 18 hours to 6 days post 20 μm ANP injection that demonstrate that large doses of polyethylene glycol ANPs do not appear to be cytotoxic.

Example 4

Preparation of GMP Loaded With Both ALA and CPT

ALA doses were selected based on the in vitro studies that were performed. The preferred form of the ALA is the free acid form. To reduce ALA release rate further, calcium salts can be prepared or ALA can be conjugated inside the NPs. If the ALA release rate needs to be increased the Na+ or K+ salt forms of ALA dispersed in the GMP matrix can be used. Further alternatively Na-RALA (the water soluble form) can be dosed orally or subcutaneously. Na-RALA can also be loaded directly into the GMP matrix (rather than into the NP) due to its water solubility.

Determination of CPT doses is provided by using FNP to encapsulate CPT into NPs or by conjugating it to the NP matrix in order to control release rate. For CPT forms with increased solubility, CPT ester prodrugs, in particular, the norvaline prodrug, are utilized (FIG. 10).

Figure 10:
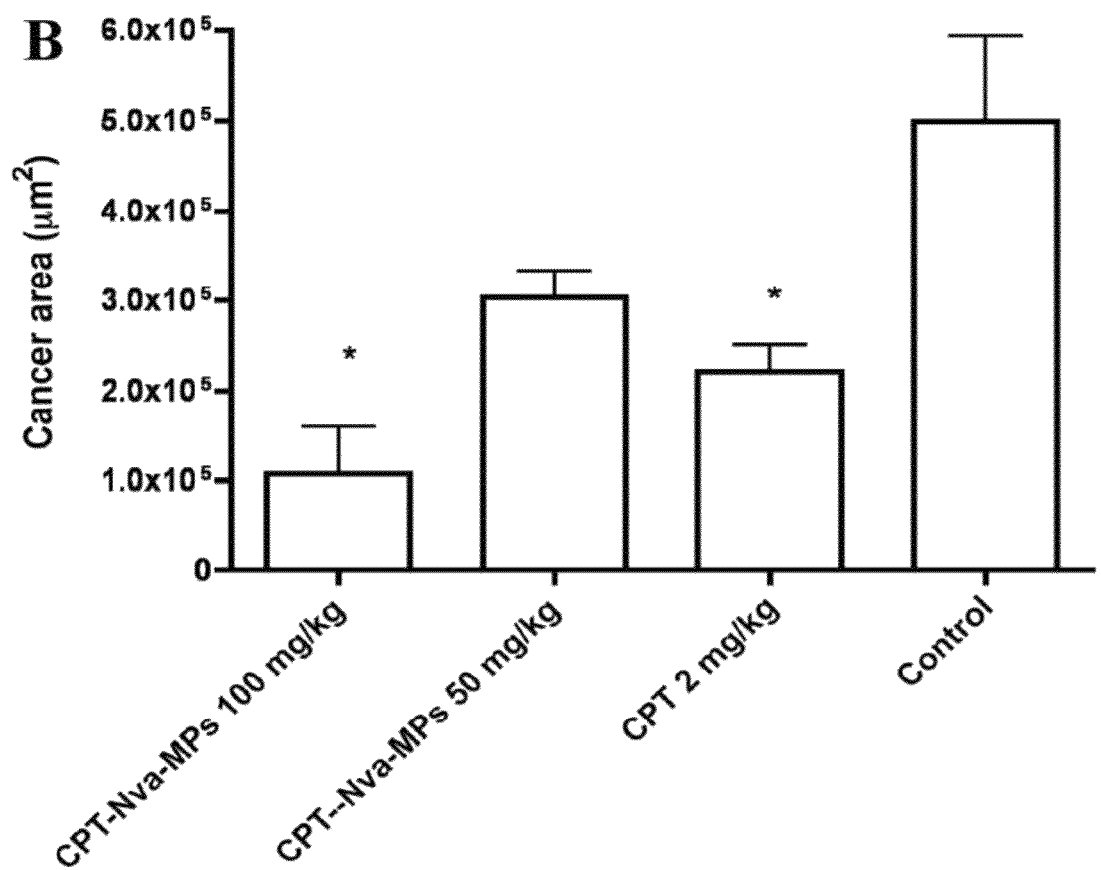
FIG. 10 provides a summary of the anti-cancer efficacy results of the treatment groups CPT-Nva-MPs (eq. CPT 0.2 mg/kg), CPT-Nva-MPs (eq. CPT 0.11 mg/kg), free CPT 2 mg/kg, and control (normal saline containing 0.1% Tween 80). Bars represent mean ±SE (n=5). *=P<0.05 compared to control.

The target GMP dose is estimated from FIG. 10. For a 250 g rat, 0.05 mg CPT is required. When using a paclitaxel loading of 38 weight percent, this requires 0.13 mg NPs. NP loading into the GMPs is at least 20% before the viscosity of the GMP aqueous phase becomes limiting. One can inject up to about 40 weight percent GMP into the tail vein of mice. Therefore, the initial GMP dose is about 0.5 mg. Using the synergy strategy through the use of CPT and ALA described above, the GMP dose is further reduced to 0.01 to 0.1 mg.

GMPs are fabricated using microfluidics and NPs loaded with CPT, ALA or CPT/ALA combinations using FNP as described above. The GMP "formulations" described above with optimal lung targeting, retention and toxicology properties serve as a starting point. CPT/ALA release is then evaluated in vitro in mouse plasma and physiological buffers at pH 6.6, 7.0 and 7.4 corresponding to tumor, lung and extracellular fluid pH.

A549 cells are cultured and passaged as previously described. The free forms of CPT and ALA, and concentration-varying combinations thereof, are evaluated in the indicated assays and combination effects are determined. Dose-response curves for CPT and ALA are constructed and IC50s determined. Combination effects are then evaluated by combining both compounds at 0.25x, 0.5x, lx, 2x, and 4x of their respective 1050s. Concentrations of CPT and ALA range from 0-106 μM and treatment times are 24, 48, 72, 96 hrs, 5 days, and 6 days.

GMPs containing CPT, ALA and CPT/ALA combinations at optimal cytotoxic ratios are tested in the orthotopic NSCLC murine model. Negative controls include solvent only and non-treated animals. Treatments start at 1 week after tumor injection, and repeated weekly for 3 weeks. Efficacy is evaluated by examining the primary tumor, regional lymph node and distant metastasis including separate tumor nodule(s) in contralateral lobes. Tumor size is monitored twice-weekly using bioluminescence and fluorescence whole body imaging (IVIS, Xenogen). After gross examination, various tissues (lung, regional lymph nodes, liver, spleen, kidney, lymphoid tissue, bone, blood, and brain) are subjected to ex vivo imaging to further examine tumor distribution. The tissues are then homogenized and analyzed by luninometry and fluorometry. Apoptosis is examined by TUNEL assay. Vessel density in tumor is also assessed. Additionally, tissue samples are embedded in paraffin, sectioned, and histopathological evaluation is performed.

NPs are fabricated and their surfaces functionalized with DV3. DV3 copy number and surface density is varied in order to optimize cell surface binding and retention. Ample confocal microscopic, biochemical and functional evidence shows that CXCR4 molecules are clustered together in lipid rafts. Therefore, without the guide from a docking exercise but with the knowledge of CXCR4 clustering, the distance between centers of juxtaposed CXCR4 molecules on cell surface is estimated to be about 3 nM by taking a cue from the distance between dimerized transferrin receptors (TfRs) of about 10 nM. Two linkers each with 15 carbon atoms are long enough to reach two juxtaposed CXCR4 molecules. The length introduces several σ-bonds between carbon atoms in the linker, resulting in free 3D rotation of the DV3 at the end of the linker and good fitting of DV3 to CXCR4. All DV3 peptides are placed close to each other at one end of the nanocarrier to minimize potential cell clustering. A battery of cell lines that differentially express CXCR4 and CXCR7 are used to determine DV3-NP binding specificity and cell surface retention properties including: (1) A549 human lung epithelial cells (the cells used in the orthotopic model) that express CXCR4 (+) and CXCR7 (+); (2) MCF7 (human mammary gland epithelial): CXCR4 (−), CXCR7 (+); (3) HEK293 (human embryonic kidney): CXCR4 (+), CXCR7 (−); and (4) MDA-MB435S (human melanocyte): CXCR4 (−), CXCR7 (−). Uptake of DV3 nanocarriers is quantified using a fluorescent plate reader or flow cytometry. Scrambled peptide sequences are used as negative controls. Competitive binding studies are performed using CXCL12 and mAbs for CXCR4 or 7. Confocal microscopy is used qualitatively for visualizing uptake and surface binding. Quantitative confocal is performed using software analysis after image acquisition and setting identical exposures for the experimental and control cells. Nonspecific surface binding is corrected using an established acid-wash procedure.

Example 5

The free forms of ALA, DV3, and DOXY, and concentrations-varying combinations thereof, are evaluated in the indicated metastasis assays and combination effects are determined using design and methods described above. Negative controls include solvent only and non-treated animals. Dose-response curves for ALA, DV3-NPs, and DOXY are constructed and IC50s determined. In addition, two agent combinations (CPT+ALA, CPT+DV3−NP, and CPT+DOXY) are studied as the final delivery system includes CPT. Combination effects are evaluated by combining compounds at 0.25x, 0.5x, 1x, 2x and 4x of their respective IC50s. In order to avoid the confounding effect of ALA cytotoxicity, the highest concentration used is non-cytotoxic. Treatment times are 24 and 48 hours. The following metastasis assays are utilized: (1) Cell Migration to assess the ability of the agent to inhibit cell migration towards a chemoattractant; (2) Cell Invasion to assess the cell's ability to invade through the extracellular matrix towards the chemoattractant, which include FBS and CXCL12; and (3) Western Blotting to measure the pro-metastatic factors ERK, NF-κB, and MMP-9.

Example 6

Figure 9:
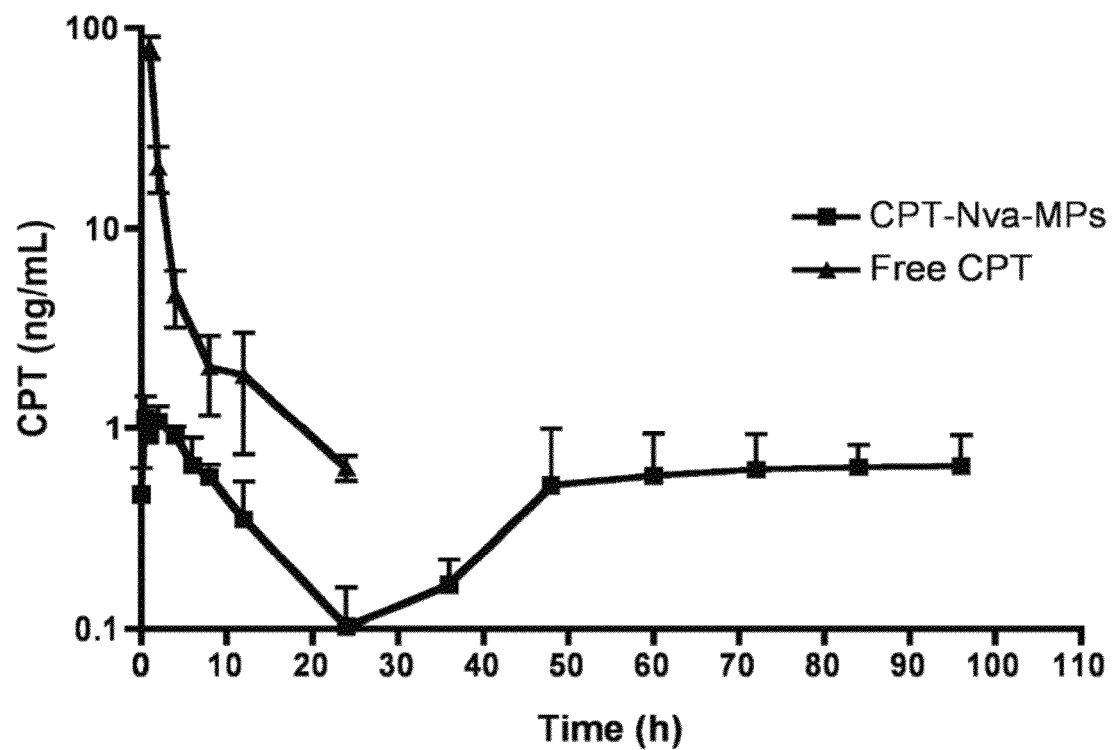
FIG. 9 shows systemic (plasma) concentration of camptothecin (CPT) as a function of time after a single bolus IV injection of CPT-Nva-MPs (CPT dose=0.2 mg/kg) (squares) and free CPT (2 mg/kg) (triangles). Values are reported as mean ±SD.

Passive pulmonary targeting of CPT using MPs increases in vivo potency/efficacy by about 10× and reduces the number of cancerous areas more significantly than IV injection of free CPT. This was determined by preparing PEGylated 6 μm polystyrene MPs with three copies of the norvaline (Nva) α-amino acid prodrug of CPT. In vivo CPT plasma concentrations were low (~1 ng/mL or less) and constant over a period of 4 days after a single IV injection of CPT-Nva-MPs as compared to high but short-lived systemic exposures after an IV injection of free CPT (FIG. 9). This demonstrates MP delivery achieves high local CPT concentrations in the lung. Anti-cancer efficacy was evaluated in an orthotopic rat lung cancer model and compared to a bolus injection of CPT. One week after A549 cell inoculation, nude rats were injected IV with CPT-Nva-MPs (50 and 100 mg/kg equivalent to CPT at 0.11 mg/kg and 0.22 mg/kg), free CPT (2 mg/kg) or vehicle control (saline containing 0.1% Tween 80).

The treatment was conducted every 3 days for 27 days. The day after the last treatment, all animals were euthanized, and organs (lung, heart, liver, spleen and liver) were dissected and weighed. The organs were fixed in 10% neutral buffered formalin for H & E staining. Animals receiving either free CPT or CPT-Nva-MPs (0.2 mg/kg CPT) were found to have smaller areas of lung cancer (p<0.05, p<0.01 respectively) than untreated animals (FIG. c-10). In addition, 40% of the animals receiving CPT-Nva-MPs (0.22 mg/kg) were free of cancer. This demonstrates that passive pulmonary targeting of CPT: (1) resulted in exceptionally low systemic CPT exposure (equivalent to CPT blood levels after 7 elimination half-lives. To put this in perspective a drug is considered to be eliminated from the body after 4-5 half-lives), (2) a significant reduction in cancerous areas in the lung, and (3) allowed for a 10-fold lower dose as compared to IV administration of free CPT.

Example 7

Figure 11:
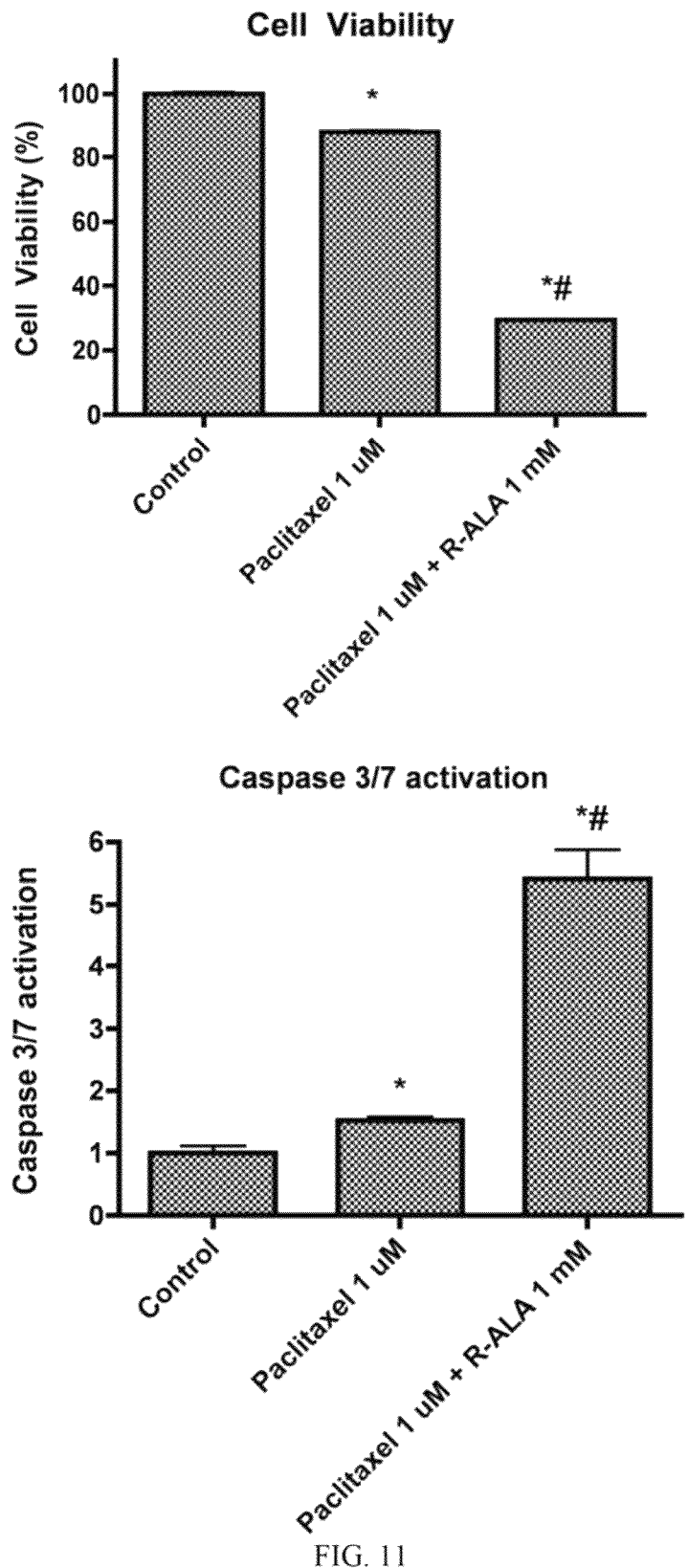
FIG. 11 (LEFT) illustrates that cells treated with paclitaxel alone showed a cell viability of 88%, whereas cells treated with paclitaxel +r-ALA showed a cell viability of 29%. Fig c-11 (RIGHT) illustrates that cells treated with paclitaxel alone showed a 1.5-fold caspase 3/7 activation relative to controls, whereas cells treated with paclitaxel +R-ALA showed a 5.4-fold caspase 3/7 activation relative to controls. *=p<0.05 relative to control. #=p<0.05 relative to paclitaxel alone.
Figure 12:
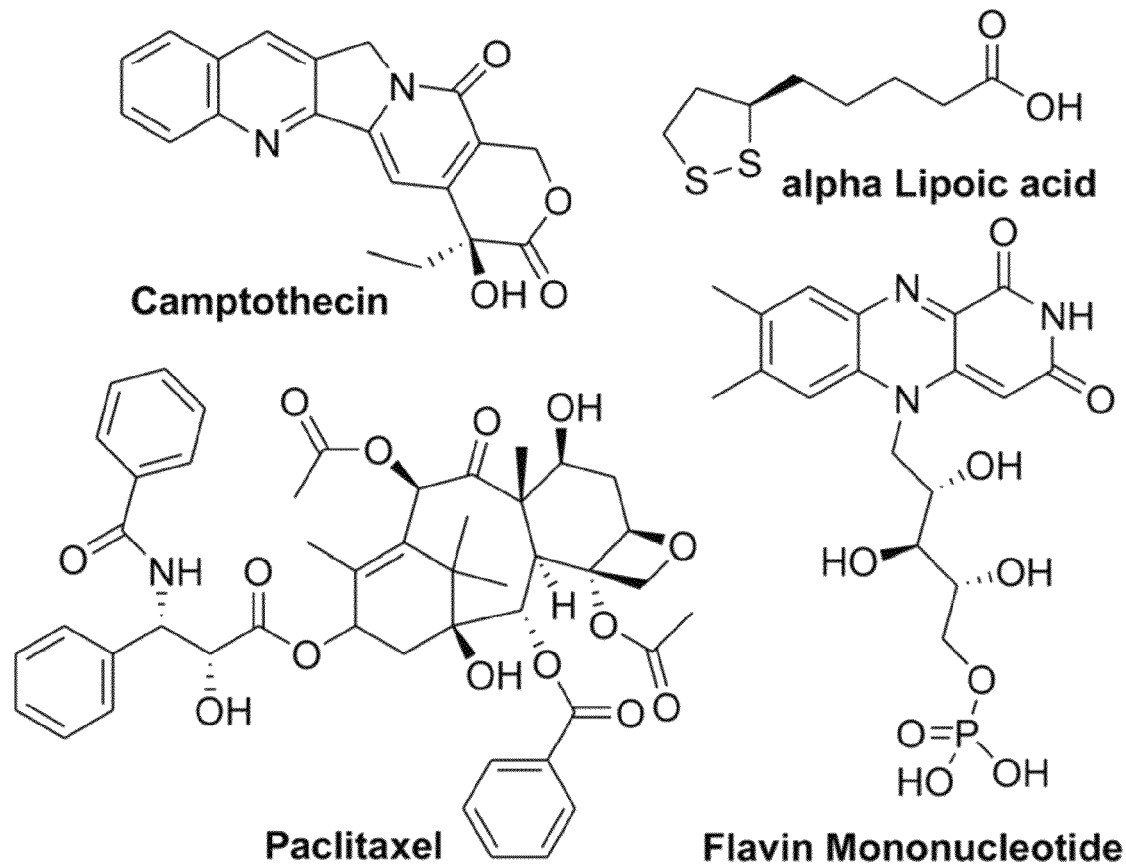
FIG. 12 illustrates structures of lung cancer drugs Camptothecin and Paclitaxel, and chemopotentiators alpha Lipoic acid and Flavin Mononucleotide.

Applicants determined that R-ALA sensitizes A549 human non-small lung adeno-carcinoma cells to the cytotoxic effects of paclitaxel. Cell viability (FIG. 11—left) and caspase 3/7 activation (apoptosis) (FIG. 11—right) of A549 cells were evaluated in response to a low dose (~EC5-EC20) of paclitaxel alone (1 μM), low dose paclitaxel +R-ALA (1 mM) or a solvent control (0.1% DMSO). Cell viability was determined with AlamarBlue® assay. Caspase 3/7 activation was determined as a measure of apoptosis using a fluorometric assay kit (Biovision, Mountain View, Calif.). A549 cells were treated with solvent control (0.1% DMSO), 1 μM paclitaxel, and 1 μM paclitaxel+1 mM R-ALA for 24 hours. FIG. c-11 (LEFT) illustrates that cells treated with paclitaxel alone showed a cell viability of 88%, whereas cells treated with paclitaxel+r-ALA showed a cell viability of 29%. FIG. c-11 (RIGHT) illustrates that cells treated with paclitaxel alone showed a 1.5-fold caspase 3/7 activation relative to controls, whereas cells treated with paclitaxel+R-ALA showed a 5.4-fold caspase 3/7 activation relative to controls. The results demonstrate that R-ALA shows potent effects on cell death and apoptosis of A549 lung carcinoma cells. Thus, the potentiating effect of R-ALA on cell death and apoptosis indicates the drug dose required for therapeutic efficacy is substantially lower, allowing for a reduction in the number of injected MPs. By reducing particle burden the potential for toxicity is further reduced.

It will be understood by those of skill in the art that numerous and various modifications can be made without departing from the spirit of the present invention. Therefore, it should be clearly understood that the various embodiments of the present invention described herein are illustrative only and not intended to limit the scope of the present invention.

We claim:

1. A method of treatment of lung cancer in a patient in need thereof comprising intravenously delivering to said patient an effective amount of a composition comprising a gel microparticle (GMP) having embedded therein a plurality of biocompatible polymeric nanoparticles wherein said biocompatible polymeric nanoparticles comprise PEG dendrons, and said particles are functionalized with targeting ligands, wherein the nanoparticles are loaded with one or more chemotherapeutic agents that are cytotoxic to lung cancer cells, and wherein said GMP have a size of at least 6 microns and a shear modulus between 4 and 200,000 Pa, wherein the size and shear modulus of said GMP are configured to provide passive delivery to a lung of said patient.

2. The method of claim 1, wherein a cell-surface targeting moiety for the surface of said lung cancer cells is covalently attached to the surface of said nanoparticle.

3. The method of claim 1, wherein the chemotherapeutic agent is selected from the group consisting of campothecin, Paclitaxel, Carboplatin. Vinorethine tartrate, Gemcitabine hydrochloride, Etoposide, Doxorubicin, Ifosfamide, Docetaxel, Cyclophosphamide, Methotrexate, Lomustine Topotecan hydrochloride and Cisplatin.

4. The method of claim 1 wherein the nanoparticies are loaded with one or more chemopotentiators for at least one of said chemotherapeutic agents.

5. The method of claim 1 wherein said nanoparticles are surface-functionalized with ligands targeted to bind with one or more prognetastatic chef signaling factor receptors on said lung cancer cells.

6. The method of claim 1 wherein the lung cancer is non-small cell lung cancer (NSCLC).

7. The method of claim 5 wherein the lung cancer is NSCLC and the ligand is DV3.

8. The method of claim 5 wherein the pro-metastatic signaling factor is selected from the group consisting of nuclear factor kappa-light-chain-enhancer of activated B cells, extracellular-signal-regulated kinases, and matrix metallopeptidase 9.

9. The method of claim 4 wherein said one or more chemotherapeutic agent, said chemopotentiator, or both are covalently attached to the interior of or the surface of the polymeric nanoparticle carrier.

10. The method of claim 4 wherein said polymeric nanoparticle carrier, said chemo-therapeutic agent and said chemopotentiator are physically admixed by flash nano-precipitation.

11. The method of claim 4, wherein the chemopotentiator is alpha-lipoic acid and the chemotherapeutic agent is selected from the group consisting of carnpothecin, Paclitaxel, Carboplatin, Vinorelbine tartra e , Gemcitabine hydrochloride, Etoposide, Doxorubicin, Ifosfamide, Docetaxel, Cyclophosphamide, Methotrexate, Lomustine (CCNU), Topotecan hydrochloride, and Cisplatin.

12. The method of claim 4, wherein said one or more chemopotentiator and one or more chemotherapeutic agent are physically admixed with the biocompatible polymeric nanoparticle.

13. The method of claim 4, wherein the chemopotentiator is selected from the group consisting of alpha-lipoic acid, alpha-lipoic acid analogues, sodium-r-alpha lipoate, dichloroacetate, carnosine, flavin mononucleotide, flavin adenine dinucleotide, ubiquinone, idebenone, mitochondria uncouplers, emthylsulfonylmethane, monophenols, flavonoids, phenolic acids, hydroxycinnamic acids, lignans, tyrosol esters, carotenoids, monoterpenes, saponins, lipids, betalains, organosalides, indoles, glucosinolates, sulfur compounds, organic acids, tocohperols, tocotrienols, vitamin D, vitamin D analogues, potassium iodide, iodine, selenium, zinc, aspirin, ibuprofen, naproxen, indomethacin, celecoxib, sulindac, diclofenac. eicosapentaenoic acid, docosabexaenoic acid, alpha linolenic acid, gamma linolenic acid, ricinoleic acid, curcumin, resveratrol, quercetin, lutein, and lycopene.

\* \* \* \* \*